(12) United States Patent
Ragini et al.

(10) Patent No.: US 8,877,349 B2
(45) Date of Patent: Nov. 4, 2014

(54) ORGANOMETALLIC COMPLEX AND ORGANIC ELECTROLUMINESCENCE DEVICE USING THE SAME

(75) Inventors: Das Rupasree Ragini, Suwon-si (KR); Che-Un Yang, Suwon-si (KR); Young-Hun Byun, Yongin-si (KR); O-Hyun Kwon, Seoul (KR); Lyong-Sun Pu, Suwon-si (KR); Shinichiro Tamura, Seongnam-si (KR); Woon-Jung Paek, Yongin-si (KR); Myeong-Suk Kim, Suwon-si (KR); Hee-Kyung Kim, Anyang-si (KR); Jong-Jin Park, Yongin-si (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 1267 days.

(21) Appl. No.: 11/640,330

(22) Filed: Dec. 18, 2006

(65) Prior Publication Data

US 2007/0178332 A1 Aug. 2, 2007

(30) Foreign Application Priority Data

Feb. 2, 2006 (KR) ........................ 10-2006-0010058

(51) Int. Cl.
*H01L 51/54* (2006.01)
*C09K 11/06* (2006.01)
*C07F 15/00* (2006.01)
*H01L 51/00* (2006.01)
*H01L 51/50* (2006.01)

(52) U.S. Cl.
CPC .... *H01L 51/0085* (2013.01); *C09K 2211/1007* (2013.01); *C09K 2211/1044* (2013.01); *H01L 51/0037* (2013.01); *C09K 2211/1011* (2013.01); *C09K 2211/185* (2013.01); *C07F 15/0033* (2013.01); *H01L 51/0042* (2013.01); *H01L 51/0081* (2013.01); *H01L 51/5016* (2013.01); *C09K 11/06* (2013.01); *C09K 2211/1029* (2013.01); *Y10S 428/917* (2013.01)
USPC .... 428/690; 428/917; 313/504; 257/E51.044; 546/5

(58) Field of Classification Search
USPC .......................................................... 546/5
See application file for complete search history.

(56) References Cited

U.S. PATENT DOCUMENTS

| 6,936,716 | B1 | 8/2005 | Lin |
| 2001/0019782 | A1 | 9/2001 | Igarashi et al. |
| 2003/0152802 | A1 | 8/2003 | Tsuboyama et al. |
| 2004/0124766 | A1 | 7/2004 | Nakagawa et al. |
| 2004/0249157 | A1 | 12/2004 | Guram et al. |
| 2005/0119485 | A1 | 6/2005 | Brown et al. |
| 2005/0175860 | A1 | 8/2005 | Kim et al. |
| 2005/0287391 | A1 | 12/2005 | Chang et al. |
| 2007/0176542 | A1* | 8/2007 | Ragini et al. .................. 313/504 |
| 2007/0196689 | A1* | 8/2007 | Ragini et al. .................. 428/690 |

FOREIGN PATENT DOCUMENTS

| CN | 1474826 A | 2/2004 |
| CN | 1626540 A | 6/2005 |
| JP | 2001-247859 A | 9/2001 |
| JP | 2004-174838 | 6/2004 |
| JP | 2005-200416 | 7/2005 |
| KR | 10-2006-0000776 A | 1/2006 |

OTHER PUBLICATIONS

M. A. Baldo et al., "Excitonic singlet-triplet ratio in a semiconducting organic thin film", Physical Review B, vol. 60, No. 20, pp. 14 422-140428, Nov. 1999.
M. A. Baldo et al., "Highly efficient phosphorescent emission from organic electroluminescent devices", Nature, vol. 395, Sep. 1998, pp. 151-154.
F. O. Garces et al., "Synthesis, Structure, Electrochemistry, and Photophysics of Methyl-Substituted Phenylpyridine Ortho-Metalated Iridium(III) Complexes", Inorg. Chem. 1988, 27, 3464-3471.
S. Sprouse, et al., "Photophysical Effects of Metal-Carbon σ Bonds in Ortho-Metalated Complexes of Ir(III) and Rh(III)", J. Am. Chem. Soc. 1984, 106, 6647-6653.
Japanese Office action issued by Japanese Patent Office on Jul. 31, 2012 in the examination of the Japanese Patent Application No. 2007-036903 which was cited in the corresponding cross-referenced U.S. Appl. No. 11/640,289 in Information Disclosure Statement filed on Sep. 20, 2012.
Slater, Jonathatn W. Rourke Jonathan P., Cyclometalated nitrogen heterocyles, Journal of Organometallic Chemistry, 2003, 668(1-2), 112-120; which was cited in the corresponding cross-referenced U.S. Appl. No. 11/640,289 in Information Disclosure Statement filed on Sep. 20, 2012.

(Continued)

*Primary Examiner* — Marie R. Yamnitzky
(74) *Attorney, Agent, or Firm* — Robert E. Bushnell, Esq.

(57) ABSTRACT

Provided are an organometallic complex providing highly efficient phosphorescence and an organic electroluminescence device using the same. The organometallic complex can be used to form an organic layer of the organic electroluminescence device, efficiently emits light of a wavelength corresponding to red light, and has high brightness and low operating voltage. The organometallic complex is represented by Formula (1)

(1)

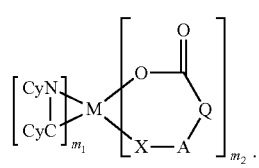

11 Claims, 4 Drawing Sheets

(56) References Cited

OTHER PUBLICATIONS

Xu, Maoliang, Li, Wenlian, An, ZhongWei, Zhou, Qun, Wang, Geyang, Crystal structure of iridium (III) bis (2-(p-biphenylyl) quinolyl-N, C2') acetylacetonate, (bpq) 2lr(acac), X-Ray Structure Analysis Online, 2005, 21(11), x185-186 which was cited in the corresponding cross-referenced U.S. Appl. No. 11/640,289 in Information Disclosure Statement filed on Sep. 20, 2012.

Korean Registration Determination Certificate issued by KIPO on Nov. 7, 2012 in the corresponding Korean Patent Application No. 10-2006-0010058.

Chinese Office Action issued by Chinese Patent Office on Jan. 26, 2011 corresponding to Chinese Patent Application No. 200610143361.7 and Request for Entry of the Accompanying Office Action attached herewith.(Cited in the corresponding cross-referenced U.S. Appl. No. 11/640,289 in Information Disclosure Statement filed on Apr. 15, 2011.).

* cited by examiner

ORGANOMETALLIC COMPLEX AND ORGANIC ELECTROLUMINESCENCE DEVICE USING THE SAME

CROSS-REFERENCE TO RELATED PATENT APPLICATION AND CLAIM OF PRIORITY

This application claims the benefit of Korean Patent Application No. 10-2006-0010058, filed on Feb. 2, 2006, in the Korean Intellectual Property Office, the disclosure of which is incorporated herein in its entirety by reference.

BACKGROUND OF THE INVENTION

1. Field of the Invention

The present invention relates to an organometallic complex and an organic electroluminescence device, and more particularly, to an organometallic complex enabling red light emission and an organic electroluminescence device including an organic layer formed of the organometallic complex.

2. Description of the Related Art

Organic electroluminescent (EL) devices, which are active display devices, use the recombination of electrons and holes in a fluorescent or phosphorescent organic compound thin layer (hereinafter, referred to as 'organic layer') to emit light when current is applied thereto. Organic electroluminescent devices are lightweight, have wide viewing angles, produce high-quality images, and can be manufactured using simple processes. Organic electroluminescent devices also can produce moving images with high color purity while having low consumption power and low voltage. Accordingly, organic electroluminescent devices are suitable for portable electronic applications.

In general, an organic electroluminescent device includes an anode, a hole transport layer, an emission layer, an electron transport layer, and a cathode sequentially stacked on a substrate. The hole transport layer, the light emitting layer, and the electron transport layer are organic layers formed of organic compounds. The organic electroluminescent device may operate as follows. When a voltage is applied between the anode and the cathode, holes emitted by the anode move to the light-emitting layer via the hole transport layer. Electrons are emitted by the cathode and move to the light-emitting layer via the electron transport layer. In the light-emitting layer, the carriers recombine to produce excitons. The excitons radiatively decay, emitting light corresponding to a band gap of the light-emitting layer.

Materials that can be used to form the light-emitting layer of the organic electroluminescent device are divided, according to the emission mechanism, into fluorescent materials using singlet excitons and phosphorescent materials using triplet excitons. The light-emitting layer is formed by such fluorescent materials or phosphorescent materials themselves or by doping such fluorescent materials or phosphorescent materials on appropriate host materials. When electrons are excited, singlet excitons and triplet excitons are generated in a host in the generation ratio of 1:3 (Baldo, et al., Phys. Rev. B, 1999, 60, 14422).

When fluorescent materials are used to form the light-emitting layer in the organic electroluminescent device, triplet excitons that are generated in the host cannot be used. However, when phosphorescent materials are used to form the light emitting layer, both singlet excitons and triplet excitons can be used, and thus, an internal quantum efficiency of 100% can be obtained (see Baldo et al., Nature, Vol. 395, 151-154, 1998). Accordingly, the use of phosphorescent materials brings higher light emitting efficiency than use of fluorescent materials.

When a heavy metal, such as Ir, Pt, Rh, or Pd is included in an organic molecule, spin-orbit coupling occurs due to a heavy atom effect, and thus, singlet states and triplet states are mixed, allowing a forbidden transition to occur and thus effectively emitting phosphorescent light even at room temperature.

As described above, transition metal compounds that include a transition metal such as Iridium (Ir) and platinum (Pt) have been developed to provide highly efficient phosphorescent materials that use a phosphorescence effect. However, development of red phosphorescent materials for full-color display device is still required.

SUMMARY OF THE INVENTION

The present invention provides an organometallic complex, which can efficiently emit light of a wavelength corresponding to red light.

The present invention also provides an organic electroluminescence device using the organometallic complex.

According to an aspect of the present invention, there is provided an organometallic complex comprising a compound represented by Formula 1:

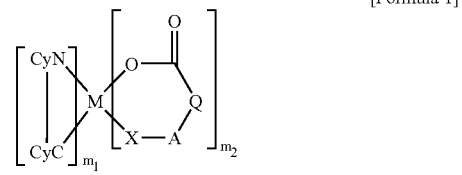

[Formula 1]

where M is Ir, Os, Pt, Pb, Re, Ru or Pd;

CyN is a substituted or unsubstituted $C_3$-$C_{60}$ heterocyclic group including nitrogen, which is combined with M, or a substituted or unsubstituted $C_3$-$C_{60}$ heteroaryl group including nitrogen, which is combined with M;

CyC is a substituted or unsubstituted $C_4$-$C_{60}$ cyclic group including carbon, which is combined with M, a substituted or unsubstituted $C_3$-$C_{60}$ heterocyclic group including carbon, which is combined with M, a substituted or unsubstituted $C_3$-$C_{60}$ aryl group including carbon, which is combined with M, or a substituted or unsubstituted $C_3$-$C_{60}$ heteroaryl group including carbon, which is combined with M;

CyN-CyC indicates a cyclometalating ligand which is combined with M through the nitrogen (N) of the CyN and the carbon (C) of the CyC;

$m_1$ is an integer in a range of 0 to 2;

$m_2$ is 3-$m_1$;

X is $NR_0$, O, or S, where $R_0$ is hydrogen, a halogen atom, a carboxyl group, or a $C_1$-$C_{20}$ alkyl group;

A indicates a single bond or a double bond; and

Q is a substituted or unsubstituted $C_6$-$C_{50}$ arylene group or a substituted or unsubstituted $C_3$-$C_{50}$ heteroarylene group.

The compound represented by Formula 1 may be represented by Formula 2.

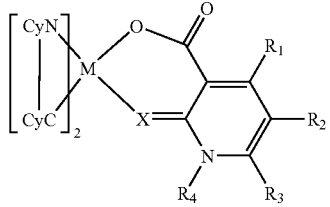

[Formula 2]

where M, X, CyN, and CyC are defined as in above; and $R_1$, $R_2$, $R_3$, and $R_4$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group and at least two of $R_1$, $R_2$, $R_3$, and $R_4$ may be fused into a 5 to 7-membered ring.

The compound represented by Formula 1 may be represented by Formulas 3 or 4:

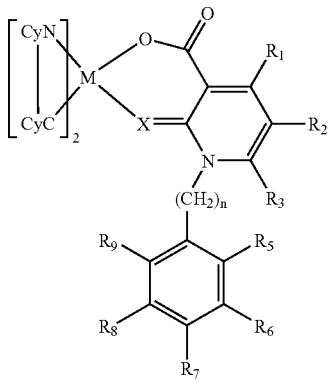

[Formula 3]

where M, X, CyN, and CyC are defined as in above, $R_1$, $R_2$, $R_3$, $R_5$, $R_6$, $R_7$, $R_8$, and $R_9$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group and at least two of $R_1$, $R_2$, $R_3$, $R_5$, $R_6$, $R_7$, $R_8$, and $R_9$ may be fused into a 5 to 7-membered ring; and n is an integer in a range of 0 to 30;

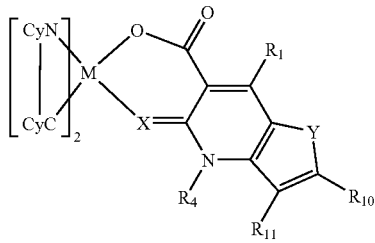

[Formula 4]

where M, X, CyN, and CyC are defined as in above; and $R_1$, $R_4$, $R_{10}$, and $R_{11}$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group, and $R_{10}$ and $R_{11}$ may be fused into a 5 to 7-membered ring; and Y is $NR_0$, O, or S, where $R_0$ is hydrogen, a halogen atom, a carboxyl group, or a $C_1$-$C_{20}$alkyl group.

The compound represented by Formula 3 may be represented by Formulas 5 through 9:

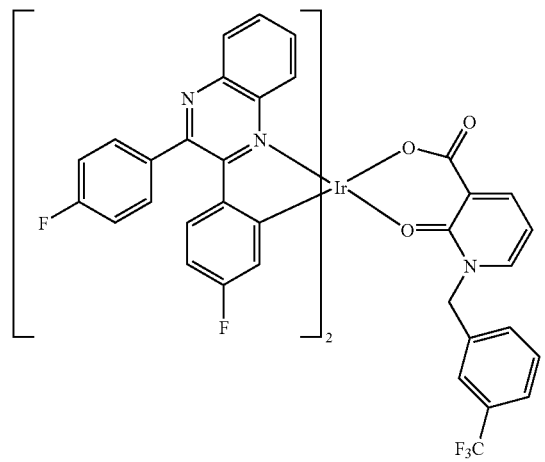

[Formula 5]

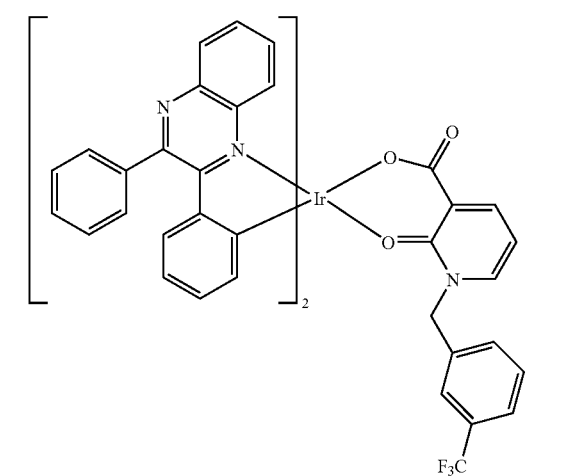

[Formula 6]

[Formula 7]

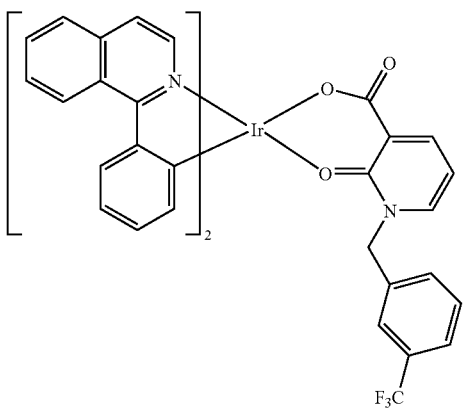

[Formula 8]

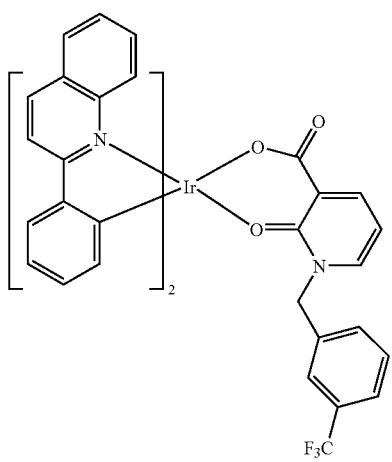

[Formula 9]

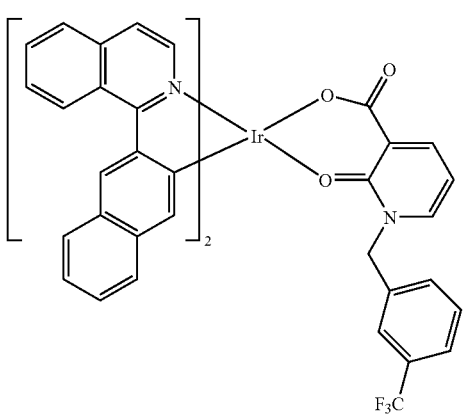

The compound represented by Formula 4 may be represented by Formulas 10 or 11:

[Formula 10]

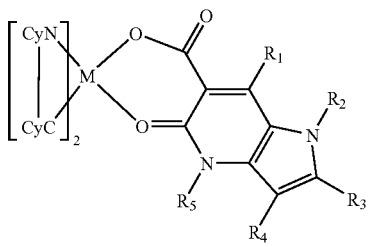

[Formula 11]

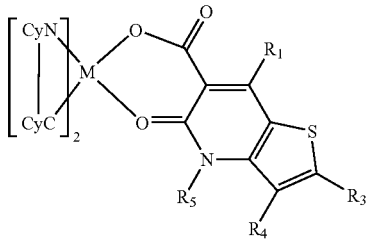

where M, CyN, and CyC are defined as in above, $R_1$, $R_2$, $R_3$, $R_4$, and $R_5$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_2$-$C_{30}$ heteroaryl group, or a substituted or unsubstituted $C_3$-$C_{30}$ heteroarylalkyl group, and $R_3$ and $R_4$ may be fused into a 5 to 7-membered ring.

According to another aspect of the present invention, there is provided an organic electroluminescence device having an organic layer interposed between a pair of electrodes, the organic layer including the organometallic complex described above.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
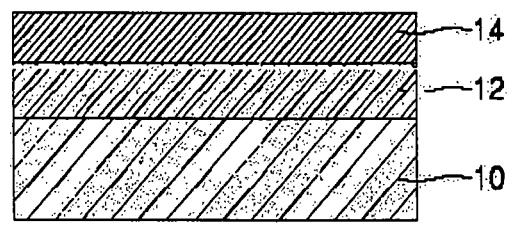
FIGS. 1a through 1f are diagrams schematically illustrating various laminated structures of an organic electroluminescent device according to embodiments of the present invention.

Hereinafter, embodiments of the present invention will be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

An embodiment of the present invention provides an organometallic complex comprising a compound represented by Formula 1, which includes an ancillary ligand formed from oxo-pyridine carboxylate. The ligand in such an organometallic complex reduces energy gap between highest occupied molecular orbital (HOMO) and triplet metal-to-ligand charge-transfer ($^3$MLCT) state to move a corresponding light emission wavelength a number of nm towards wavelengths corresponding to red light. Accordingly, emission of light of a wavelength corresponding to red light, obtained from triplet MLCT of Ir(III) complex, is available in an organic electroluminescent device including the organometallic complex. The organometallic complex comprising a compound represented by Formula 1 according to an embodiment of the present invention is shown below:

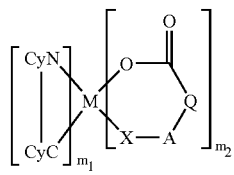

<Formula 1> where M is Ir, Os, Pt, Pb, Re, Ru or Pd;

CyN is a substituted or unsubstituted $C_3$-$C_{60}$ heterocyclic group including nitrogen, which is coordinated to M, or a substituted or unsubstituted $C_3$-$C_{60}$ heteroaryl group including nitrogen, which is coordinated to M;

CyC is a substituted or unsubstituted $C_4$-$C_{60}$ cyclic group including carbon, which is combined with M, a substituted or unsubstituted $C_3$-$C_{60}$ heterocyclic group including carbon, which is combined with M, a substituted or unsubstituted $C_3$-$C_{60}$ aryl group including carbon, which is combined with M, or a substituted or unsubstituted $C_3$-$C_{60}$ heteroaryl group including carbon, which is combined with M;

CyN-CyC represents a cyclometalating ligand which is combined with M through the nitrogen (N) of the CyN and the carbon (C) of the CyC;

$m_1$ is an integer in a range of 0 to 2;

$m_2$ is 3-$m_1$;

X is $NR_0$, O, or S, where $R_0$ is hydrogen, a halogen atom, a carboxyl group, or a $C_1$-$C_{20}$ alkyl group;

A indicates a single bond or a double bond; and

Q is a substituted or unsubstituted $C_6$-$C_{50}$ arylene group or a substituted or unsubstituted $C_3$-$C_{50}$ heteroarylene group.

In the organometallic complex of Formula 1 according to an embodiment of the present invention, M is a core metal which combines with the cyclometalating ligand and/or an ancillary ligand, for example, Ir, Os, Pt, Pb, Re, Ru or Pd. Ir or Pt may be used, but the core metal used is not limited thereto.

CyN of Formula 1 is a heterocyclic group or a heteroaryl group including a nitrogen atom, which directly forms coordinate covalent bond with a core metal, M. The heterocyclic group has a cyclic group in which one or more atoms of the ring are an element other than carbon, for example, N, O, S and/or P. Examples of the substituted or unsubstituted $C_3$-$C_{60}$ heterocyclic group of CyN are pyrrolidine, morpholine, thio-morpholine, thiazolidine, and the like, but are not limited thereto. The heteroaryl group has an aryl group in which one or more atoms of the ring are an element other than carbon, for example, N, O, S and/or P. Examples of the substituted or unsubstituted $C_3$-$C_{60}$ heteroaryl group of CyN are pyridine, 4-methoxypyridine, quinoline, pyrrole, indole, pyrazine, pyrazole, imidazole, pyrimidine, quinazoline, thiazole, oxazole, triazine, 1,2,4-triazole, and the like, but are not limited thereto.

Examples of the substituted or unsubstituted $C_4$-$C_{60}$ cyclic group including carbon which is combined with M in CyC of Formula 1 are cyclohexane, cyclopentane, and the like. Examples of the substituted or unsubstituted $C_3$-$C_{60}$ heterocyclic group including carbon which is combined with M are tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, and the like. Examples of the substituted or unsubstituted $C_4$-$C_{60}$ aryl group including carbon which is combined with M are phenyl, 1,3-benzodioxole, biphenyl, naphthalene, anthracene, azulene, and the like. Examples of the substituted or unsubstituted $C_3$-$C_{60}$ heteroaryl group including carbon which is combined with M may be thiophene, furan2(5H)-furanone, pyridine, coumarin, imidazole, 2-phenylpyridine, 2-benzothiazole, 2-benzooxazole, 1-phenylpyrazole, 1-naphthylpyrazole, 5-(4-methoxyphenyl)pyrazole, 2,5-bisphenyl-1,3,4-oxadilzole, 2,3-benzofuran2-(4-biphenyl)-6-phenyl benzooxazole, and the like.

CyN and CyC of CyN-CyC in Formula 1 may be connected to each other to form a condensed ring such as a substituted or unsubstituted 4-7 atom cyclic group or a substituted or unsubstituted $C_4$-$C_7$ atom heterocyclic group. Here, a cyclic group or a heterocyclic group refers to a C1-C30 cycloalkyl group, a C1-C30 heterocylcoalkyl group, a C6-C30 aryl group, or a C4-C30 heteroaryl group and can be substituted by one or more substituent. The term 'hetero' indicates heteroatoms such as N, O, P, S, and the like.

One or more hydrogen in the compound represented by Formula 1 can be substituted with various substituents and examples of the substituent are a halogen atom, $OR_1$, $-N(R_1)_2$, $-P(R_1)_2$, $-POR_1$, $-PO_2R_1$, $-PO_3R_1$, $-SR_1$, $-Si(R_1)_3$, $-B(R_1)_2$, $-B(OR_1)_2$, $-C(O)R_1$, $-C(O)OR_1$, $-C(O)N(R_1)$, $-CN$, $-NO_2$, $-SO_2$, $-SOR_1$, $-SO_2R_1$, $-SO_3R_1$. Here, $R_1$ is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

X is $NR_0$, O, or S, where $R_0$ is hydrogen, a halogen atom, a carboxyl group, or a $C_1$-$C_{20}$ alkyl group.

Q is a substituted or unsubstituted $C_6$-$C_{50}$ arylene group or a substituted or unsubstituted $C_3$-$C_{50}$ heteroarylene group.

$m_1$ may be an integer in a range of 0 to 2 and $m_2$ may be 3-$m_1$, preferably, $m_1$ is 1 or 2 and $m_2$ is 1 or 2, respectively. More preferably, $m_1$ is 2 and $m_2$ is 1.

The cyclometalating ligand (CyN-CyC) may be represented by one of Formulas 12 through 40, but is not limited thereto.

[Formula 12]
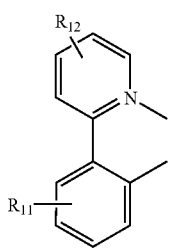
[Formula 13]
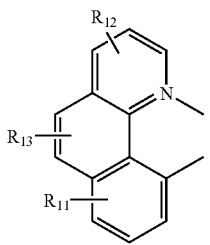
[Formula 14]
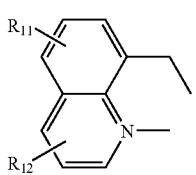
[Formula 15]
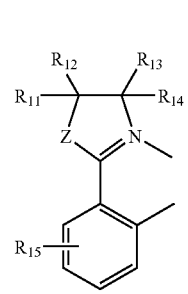
[Formula 16]
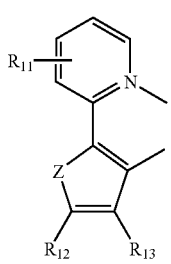
[Formula 17]
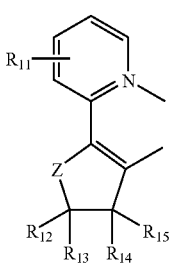
[Formula 18]
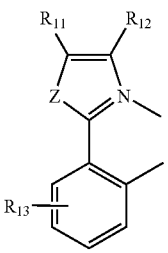
[Formula 19]
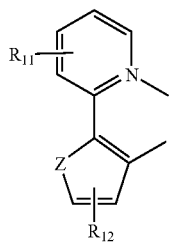
[Formula 20]
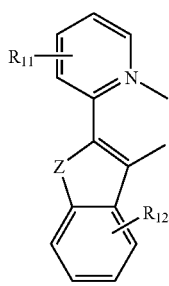
[Formula 21]
[Formula 22]
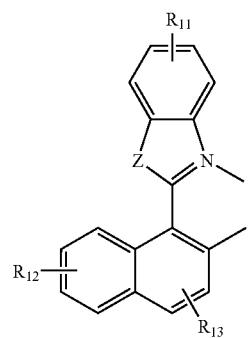

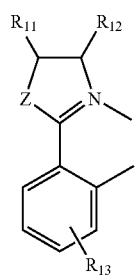 [Formula 23]
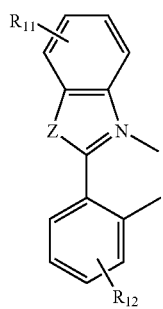 [Formula 24]
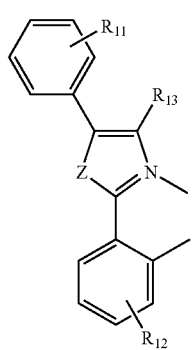 [Formula 25]
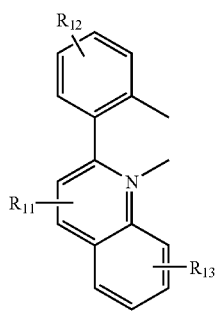 [Formula 26]
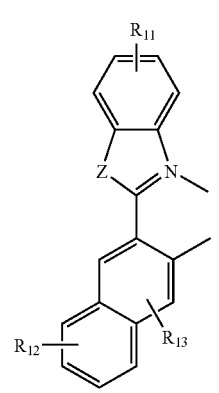 [Formula 27]
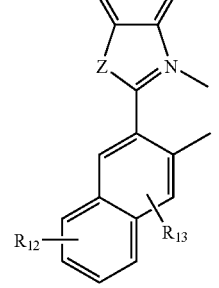 [Formula 28]
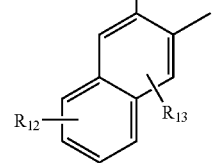 [Formula 29]
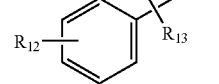 [Formula 30]
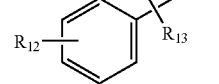 [Formula 31]
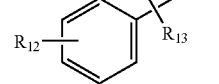 [Formula 32]

[Formula 32]
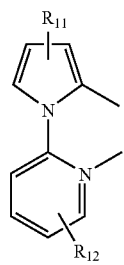

[Formula 33]
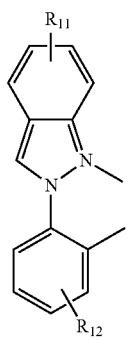

[Formula 34]
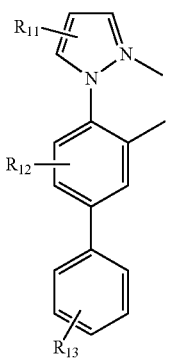

[Formula 35]
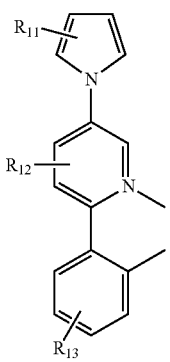

[Formula 36]
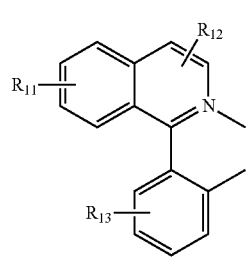

[Formula 37]
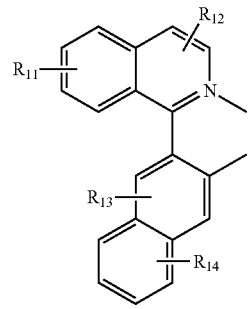

[Formula 38]
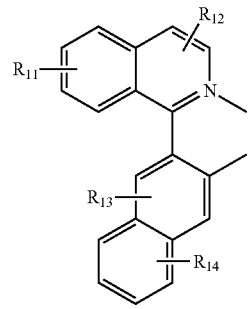

[Formula 39]
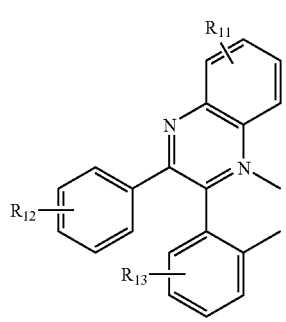

[Formula 40]
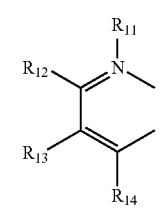

where $R_{11}$, $R_{12}$, $R_{13}$, $R_{14}$, and $R_{15}$, are each independently hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, or a $C_6$-$C_{20}$ aryl group, where R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and Z is S, O, or NR$_0$, where R$_0$ is hydrogen or a $C_1$-$C_{20}$ alkyl group.

Preferably, the organometallic complex represented by Formula 1 may represented by Formula 2.

<Formula 2>
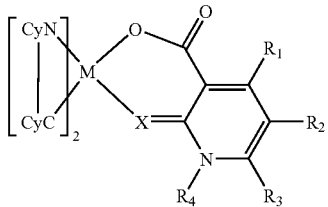

where M, X, CyN, and CyC are defined as in the previous embodiment represented by Formula 1 above; and $R_1$, $R_2$, $R_3$, and $R_4$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group and at least two of $R_1$, $R_2$, $R_3$, and $R_4$ may be fused into a 5 to 7-membered ring.

The organometallic complex of Formula 2 may be represented in more detail by Formulas 3 or 4, but is not limited thereto.

<Formula 3>

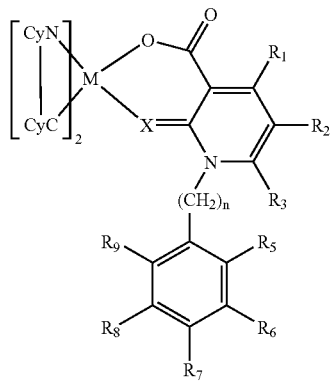

where M, X, CyN, and CyC are defined as in the previous embodiment represented by Formula 1 above;

$R_1$, $R_2$, $R_3$, $R_5$, $R_6$, $R_7$, $R_8$, and $R_9$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group, and at least two of $R_1$, $R_2$, $R_3$, $R_5$, $R_6$, $R_7$, $R_8$, and $R_9$ may be fused into a 5 to 7-membered ring; and n is an integer in a range of 0 to 30.

<Formula 4>

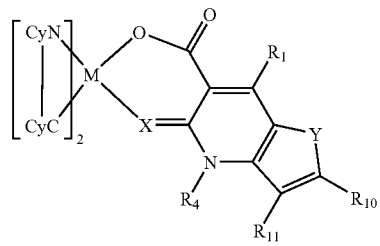

where M, X, CyN, and CyC are defined as in the previous embodiment represented by Formula 1 above; and $R_1$, $R_4$, $R_{10}$, and $R_{11}$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group. $R_{10}$ and $R_{11}$ may be fused into a 5 to 7-membered ring and Y is $NR_0$, O, or S, where $R_0$ is hydrogen, a halogen atom, a carboxyl group, or a $C_1$-$C_{20}$alkyl group.

The compound represented by Formula 3 may be represented by Formulas 5 through 9.

<Formula 5>

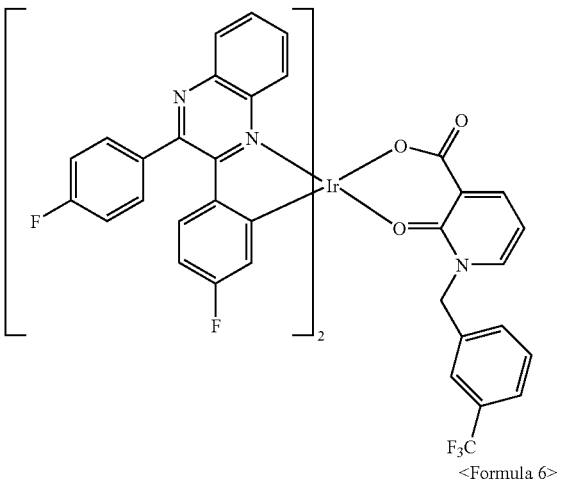

<Formula 6>

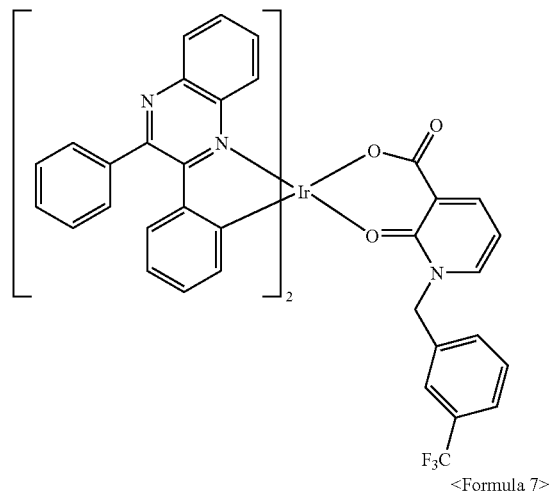

<Formula 7>

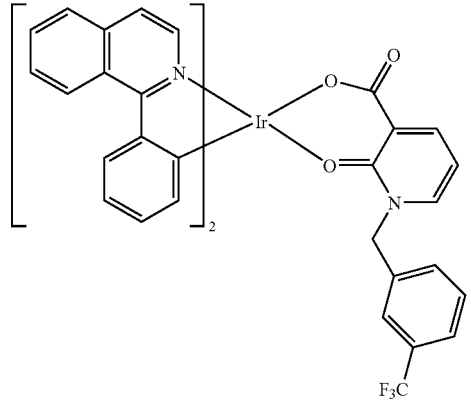

-continued

<Formula 8>

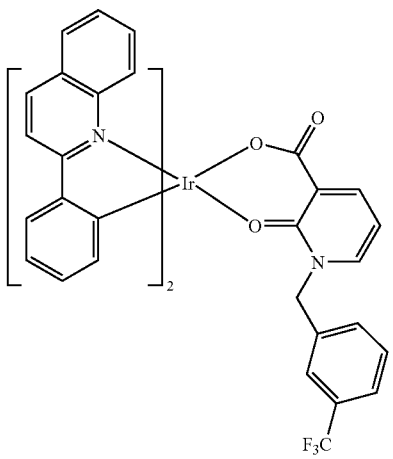

<Formula 9>

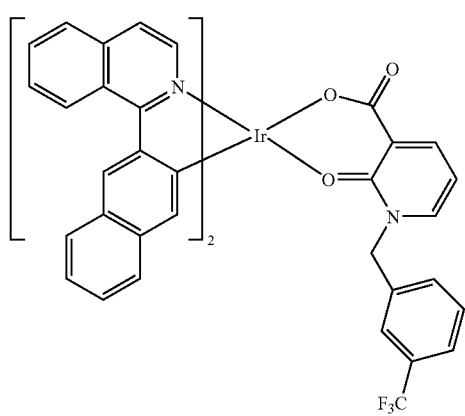

The compound represented by Formula 4 may be represented by Formulas 10 through 11.

[Formula 10]

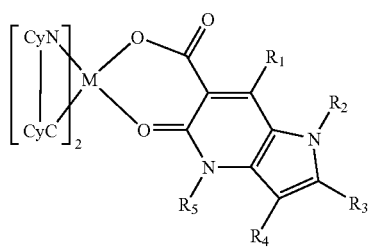

[Formula 11]

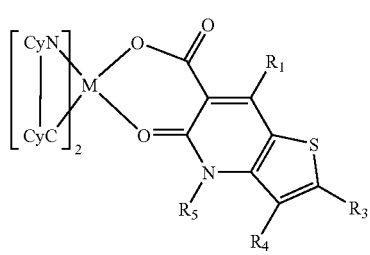

where M, X, CyN, and CyC are defined as in the previous embodiment represented by Formula 1 above; and $R_1$, $R_2$, $R_3$, $R_4$, and $R_5$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_2$-$C_{30}$ heteroaryl group, or a substituted or unsubstituted $C_3$-$C_{30}$ heteroarylalkyl group. $R_3$ and $R_4$ may be fused into a 5 to 7-membered ring.

The organometallic complex represented by Formula 1 can be synthesized using $[Ir(C^{\wedge}N)_2Cl]_2$ derivative, which is used as a starting material to provide a cyclometalating moiety, and a method disclosed by Watts Group (See F. O. Garces, R. J. Watts, Inorg. Chem. 1988, (27), 3464, which is incorporated herein by reference).

The organic electroluminescence device of the embodiment of the present invention is manufactured by using the organometallic complex of the embodiment of the present invention to form an organic layer, for example, a light emitting layer. The organometallic complex represented by Formula 1 is suitable as a phosphorescent dopant material for forming a light emitting layer and exhibits excellent emission of light of wavelengths corresponding to red light.

When the organometallic complex represented by formula 1 is used as the phosphorescent dopant, the organic layer may further include at least one host selected from the group consisting of one kind of polymer host, a mixture host comprising one or more kind of polymer host, a mixture host comprising a polymer and a small molecule, a small molecule host, and a non-emitting polymer matrix. Here, for polymer host, small molecule host, and non-emitting polymer matrix, any materials conventionally used for forming a light emitting layer of an organic electroluminescent device can be used. Examples of the polymer host are, but are not limited to, poly(vinylcarbazole) (PVK), Polyfluorene, and the like. Examples of the small molecule host are, but are not limited to, CBP(4,4'-N,N'-dicarbazole-biphenyl), 4,4'-bis[9-(3,6-biphenylcarbazolyl)]-1,1'-biphenyl, 9,10-bis[(2',7'-t-butyl)-9', 9''-spirobifluorenyl anthracene, tetrafluorene, and the like. Examples of the non-emitting polymer matrix are, but are not limited to, polymethylmethacrylate, polystyrene, and the like.

The organometallic complex represented by Formula 1 may be in an amount of 1 to 30 parts by weight based on 100 parts by weight of materials used to form the light emitting layer. When the amount is below 1 part by weight, phosphorescent materials are insufficient and thus, efficiency and lifetime thereof are reduced. When the amount is above 30 parts by weight, quenching of triplet excitons occurs and thus, efficiency is reduced. In addition, when introducing the organometallic complex to form the light emitting layer, various methods such as vacuum depositing, sputtering, printing, coating, and ink jetting can be used.

Moreover, the organometallic complex represented by Formula 1 may be used together with green phosphorescent materials or blue phosphorescent materials to realize white light.

FIGS. 1a through 1f are diagrams schematically illustrating various laminated structures of an organic electroluminescent (EL) device according to embodiments of the present invention.

Referring to FIG. 1a, an organic electroluminescent device according to an embodiment of the present invention comprises a light emitting layer 12 having an organometallic complex of Formula 1 laminated on a first electrode 10 and a second electrode 14 formed on the light emitting layer 12.

Figure 1B:
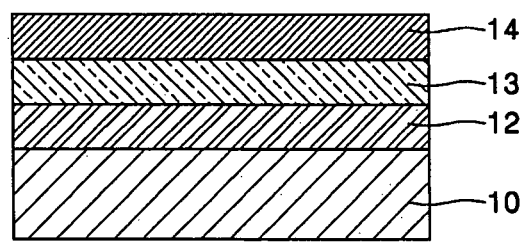

Referring to FIG. 1b, the organic electroluminescent device according to another embodiment of the present invention comprises a light emitting layer 12 having an organometallic complex of Formula 1 laminated on a first electrode 10, a hole blocking layer (HBL) 13 laminated on the light emitting layer 12, and a second electrode 14 formed on the HBL 13.

Figure 1C:
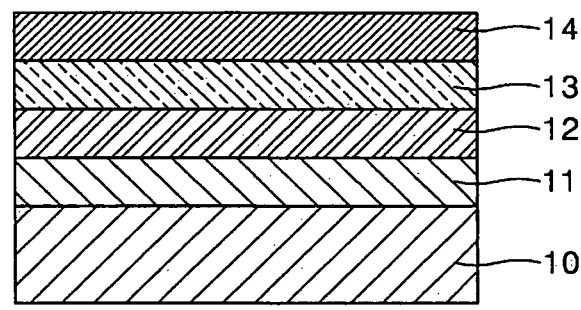

Referring to FIG. 1c, the organic electroluminescent device according to another embodiment of the present invention has the same structure as the embodiment shown in FIG. 1b except that a hole injection layer (HIL) 11 is further formed between the first electrode 10 and the light emitting layer 12.

Figure 1D:
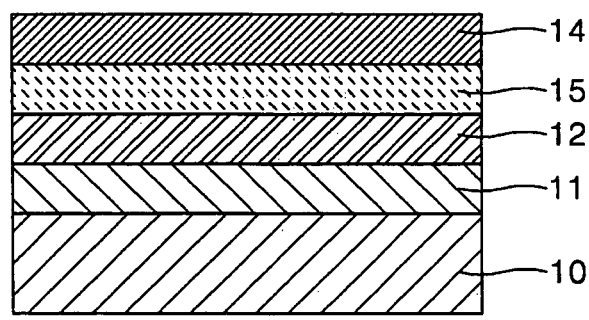

Referring to FIG. 1d, the organic electroluminescent device according to another embodiment of the present invention has the same structure as the embodiment shown in FIG. 1c except that an electron transport layer (ETL) 15 is formed on the light emitting layer 12, instead of the HBL 13.

Figure 1E:
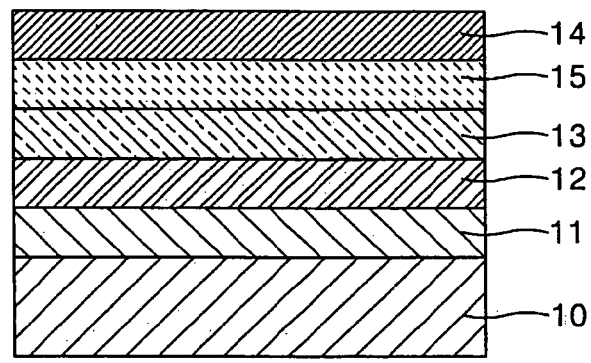

Referring to FIG. 1e, the organic electroluminescent device according to another embodiment of the present invention has the same structure as the embodiment shown in FIG. 1c except that two layers which include the HBL 13 and the ETL 15 instead of the single layered HBL 13 is formed on the light emitting layer 12 having an organometallic complex of Formula 1, wherein the HBL 13 and the ETL 15 are sequentially laminated on the light emitting layer 12. In some cases, in FIG. 1e, an electron injection layer may be further formed between the ETL 15 and the second electrode 14.

Figure 1F:
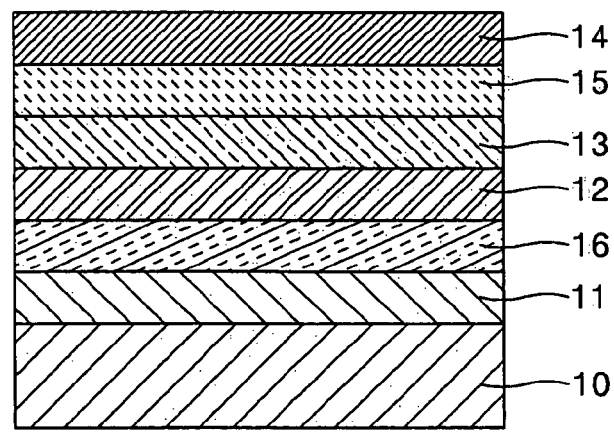

Referring to FIG. 1f, the organic electroluminescent device according to another embodiment of the present invention has the same structure as the embodiment shown in FIG. 1e except that a hole transport layer 16 is further formed between the HIL 11 and the light emitting layer 12. The hole transport layer 16 prevents impurities from penetrating into the light emitting layer 12 from the HIL 11.

The Organic EL device having the laminated structures described above may be formed using conventional fabricating methods, and the structures thereof are not particularly restricted.

The thickness of the organic layer may be in a range of 30 to 100 nm. When the thickness of the organic layer is below 30 nm, efficiency and lifetime thereof are reduced. When the thickness of the organic layer is above 100 nm, operating voltage is increased.

Here, the organic layer refers to a layer formed of organic compounds, which is formed between a pair of electrodes in an organic EL device, for example, a light emitting layer, an electron transport layer, and a hole transport layer.

In the organic EL device, a buffer layer may be interposed between each layer. The buffer layer may be formed of any materials used conventionally, for example, copper phthalocyanine, polythiophene, polyaniline, polyacetylene, polypyrrole, polyphenylene vinylene, or the derivatives thereof, but is not limited thereto.

The HTL may be formed of any materials used conventionally, for example, polytriphenylamine, but is not limited thereto.

The ETL may be formed of any materials used conventionally, for example, polyoxadiazole, but is not limited thereto.

The HBL may be formed of any materials used conventionally, for example, LiF, $BaF_2$, or $MgF_2$, but is not limited thereto.

In the manufacture of the organic EL device of the embodiment of the present invention, special equipment and method are not required. The organic EL device can be manufactured according to conventional manufacturing methods using phosphorescent materials.

The organometallic complex of Formula 1 according to the embodiment of the present invention may emit light of a wavelength in the range of 550 to 650 nm.

A light emitting diode using the organometallic complex can be used in light source illuminations for full-color displays, backlights, outdoor billboards, optical communication, and interior decoration.

The present invention will be described in greater detail with reference to the following examples. The following examples are for illustrative purposes and are not intended to limit the scope of the invention.

Reference Example 1

Synthesis of 2,3-di(4-fluoro) phenylquinoxaline iridium dimer

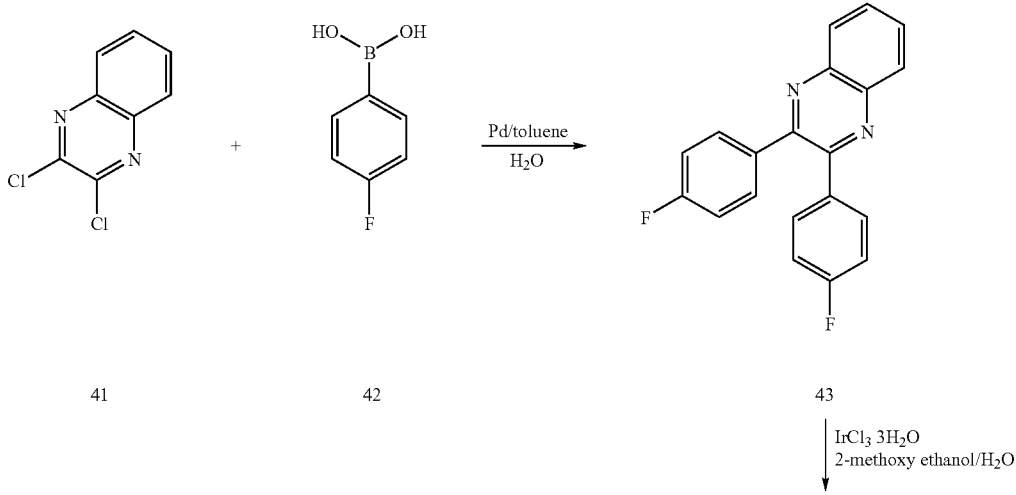

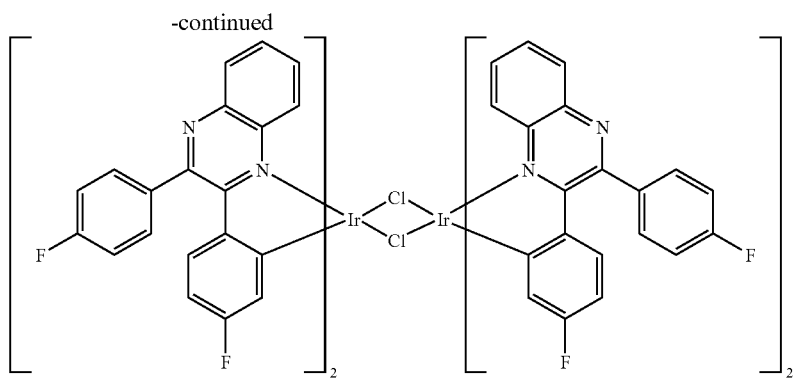

44

As illustrated in Reaction Scheme 1, a 2M sodium carbonate solution with 95 ml of water, 5 g (25 mmol) of 2,3-dichloroquinoxaline of Formula 41, 4.35 g (31 mmol) of (4-fluoro) phenyl boronic acid of Formula 42, 100 ml of toluene, and 48 ml of ethanol, was added to a 500 ml branched flask and stirred in a nitrogen atmosphere at room temperature.

Subsequently, 4.53 g (3.92 mmol) of tetrakis(triphenylphosphine)palladium(0) was added to the reaction mixture and refluxed in a nitrogen atmosphere in complete darkness for 15 hours.

After the reaction was completed, the reaction mixture was adjusted to room temperature and extracted using ethylacetate and water. The extracted resultant was separated using column chromatography (toluene:hexane=10:1) and then a liquid of 2,3-di(4-fluoro) phenylquinoxaline of Formula 43 was synthesized.

A 2,3-di(4-fluoro) phenylquinoxaline iridium dimer of Formula 44 was prepared using the 2,3-di(4-fluoro) phenylquinoxaline monomer and $IrCl_3 \cdot 3H_2O$. In this case, a synthesis method disclosed in J. Am. Chem. Soc., 1984, 106, 6647-6653 was used. The structure of the final product was analyzed using a $^1H$ NMR spectrum:

$^1$H-NMR(CD$_2$Cl$_2$,ppm): 8.26 (d, 1H), 8.17 (broad, 1H), 7.96 (broad, 1H), 7.69 (d, 1H), 7.34 (broad 1H), 7.28 (t, 2H), 6.91 (t,1H), 6.69 (t, 1H), 6.26 (t, 1H), 5.29 (d, 1H).

Reference Example 2

Synthesis of 2,3-diphenylquinoxaline iridium dimer

<Reaction Scheme 2>

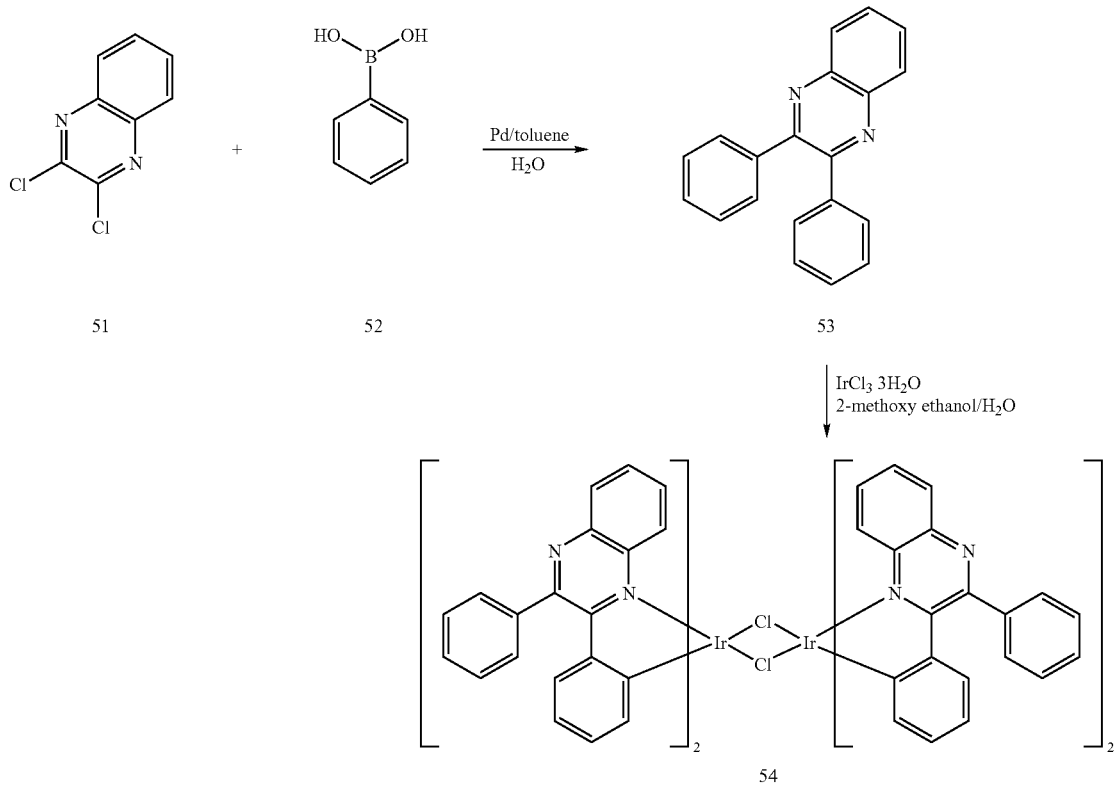

As illustrated in Reaction Scheme 2, a 2,3-diphenylquinoxaline iridium dimer of Formula 54 was synthesized in the same manner as in Reference Example 1, except that 4 g (31 mmol) of phenyl boronic acid of Formula 52 was used instead of (4-fluoro) phenyl boronic acid. The structure of the final product was analyzed using a $^1$H NMR spectrum:

$^1$H-NMR(CD$_2$Cl$_2$,ppm): 8.42 (d, 1H), 8.02 d, 2H), 7.71-7.65 (m, 4H), 7.28 (d, 1H), 6.87 (d, 1H), 6.70 (t, 1H), 6.44 (t, 1H), 6.17 (t, 1H), 5.56 (d, 1H).

Reference Example 3

Synthesis of 1-biphenylisoquinoline iridium dimer

<Reaction Scheme 3>

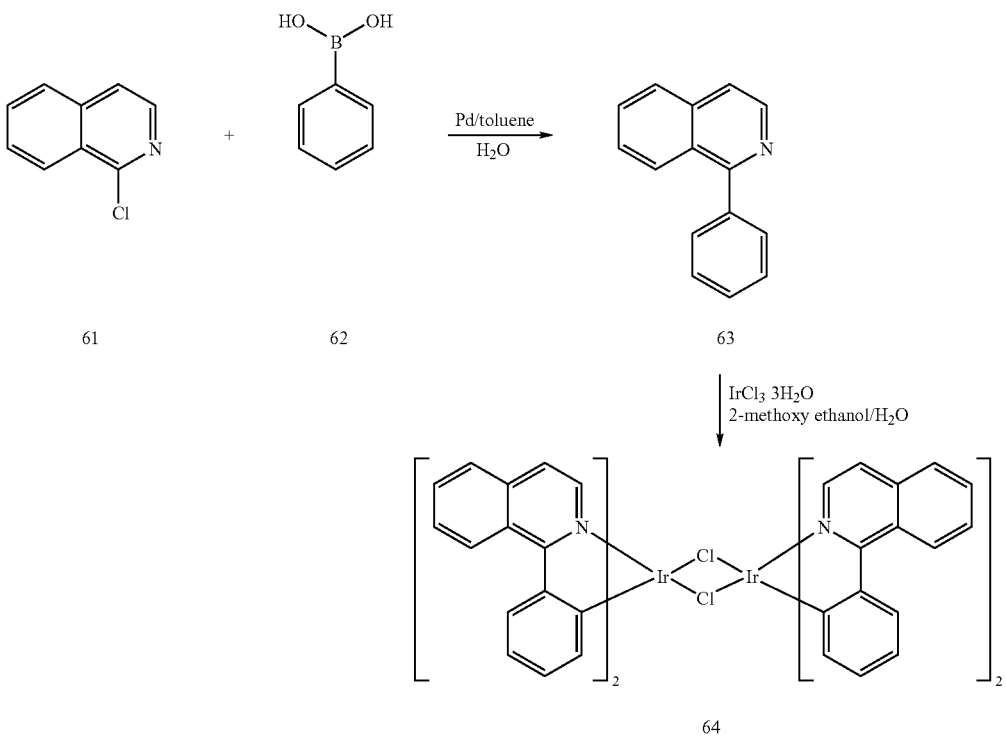

As illustrated in Reaction Scheme 3, a 1-biphenylisoquinoline iridium dimer of Formula 64 was synthesized in the same manner as in Reference Example 2, except that 5 g (31 mmol) of 1-chloroisoquinoline was used instead of 2,3-dichloroquinoxaline.

$^1$H-NMR(CD$_2$Cl$_2$,ppm): supplementation required 9.04 (d, 1H0, 8.96 (d, 1H), 8.12 (d, 1H), 7.83 (d, 2H), 7.78 (t, 2H), 6.82 (t, 1H), 6.55 (d, 1H), 6.50 (t, 1H), 6.03 (d, 1H).

Reference Example 4
Synthesis of 2-phenylquinoline iridium dimer

<Reaction Scheme 4>

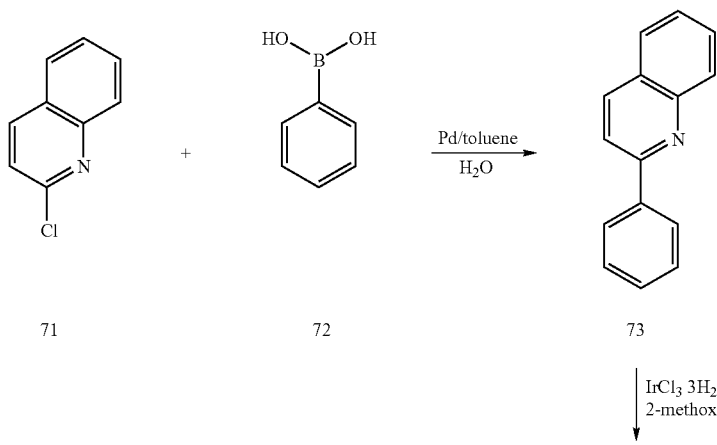

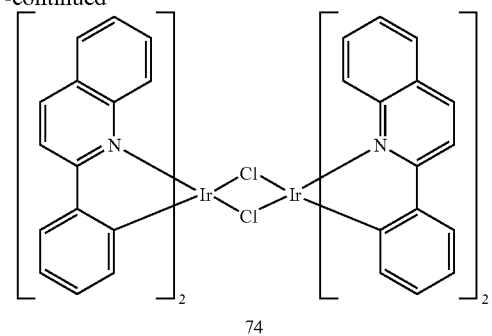

74

As illustrated in Reaction Scheme 4, a 2-phenylquinoline iridium dimer of Formula 74 was synthesized in the same manner as in Reference Example 3, except that 5 g (31 mmol) of 2-chloroquinoline was used instead of 1-chloroisoquinoline.

Reference Example 5

Synthesis of 1-naphthylisoquinoline iridium dimer

As illustrated in Reaction Scheme 5, a 1-naphthylisoquinoline iridium dimer of Formula 84 was synthesized in the same manner as in Reference Example 3, except that 6 g (30 mmol) of naphthyl boronic acid was used instead of phenyl boronic acid. The structure of the final product was analyzed using a $^1$H NMR spectrum:

$^1$H-NMR(CD$_2$Cl$_2$,ppm): 9.06 (d,2H), 9.00 (d, 1H), 8.15 (d, 1H), 8.00-7.71 (m, 4H), 6.69 (t, 1H), 6.58-6.49 (m, 2H), 6.05 (d, 1H).

<Reaction Scheme 5>

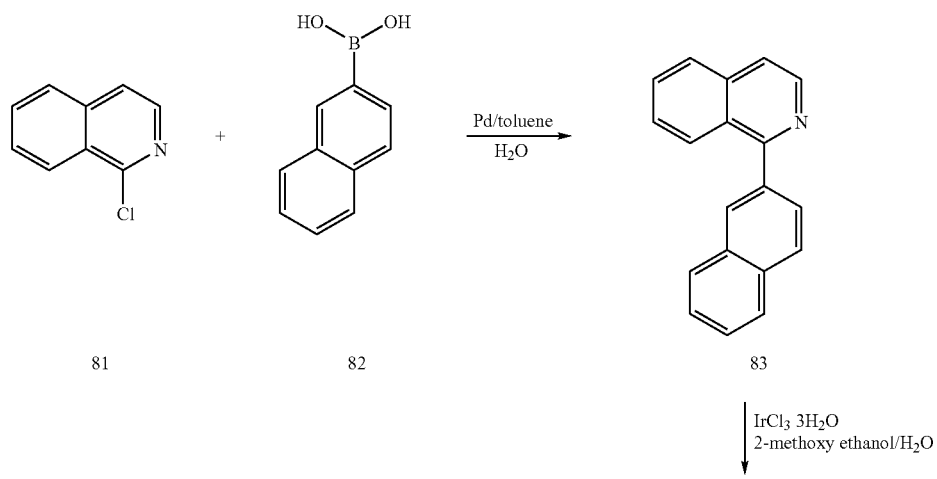

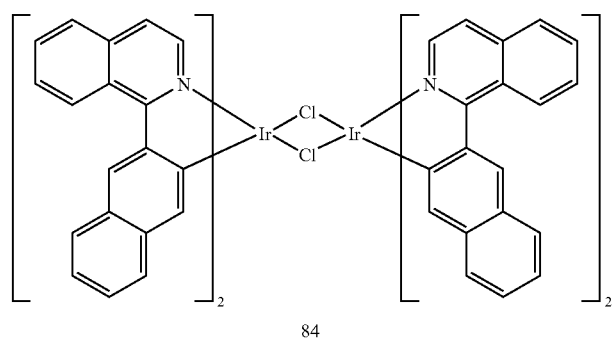

84

EXAMPLE 1

Synthesis of Compound Represented by Formula 5

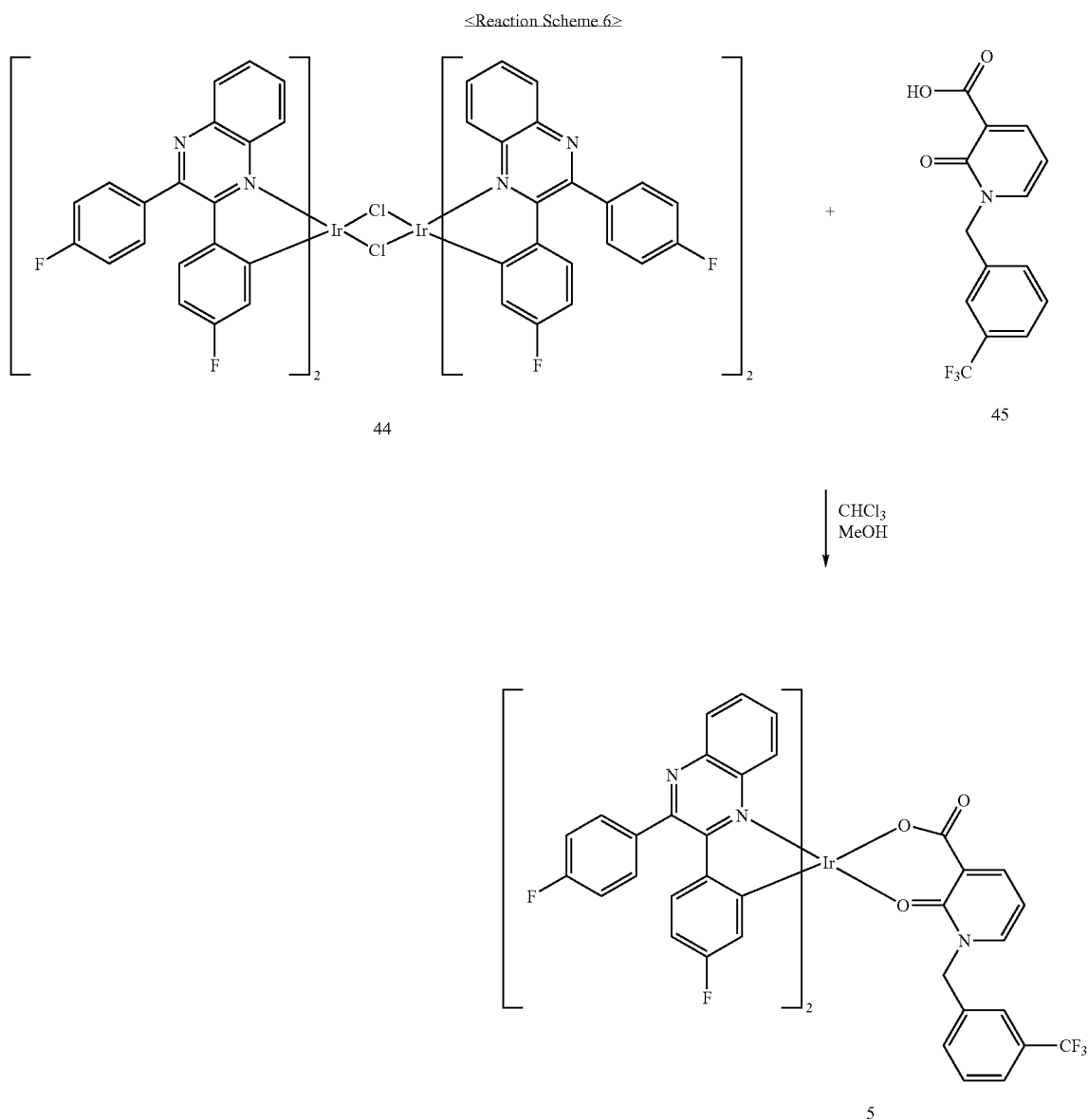

<Reaction Scheme 6>

As illustrated in Reaction Scheme 6, in a nitrogen atmosphere, 0.4 mmol of [Ir(2,3-(4-fluoro)-quinoxaline)$_2$Cl]$_2$ of Formula 44 and 0.88 mmol of 2-oxo-1-(3-trifluoromethyl-benzyl)-1,2-dihydro-pyridine-3-carboxylic acid represented by Formula 45 and 2.0 mmol of sodium carbonate were added to a 250 ml branched flask and dissolved in 40 ml of trichloromethane to react for 2 to 10 hours at room temperature. After the reaction was completed, the reaction solution was Celite filtered and precipitated in hexane to obtain the carboxylate represented by Formula 5. The obtained red solid was further purified using silica-gel column (methylenechloride:acetone=10:1). The structure of the final product was analyzed using a $^1$H NMR spectrum:

$^1$H-NMR(CDCl$_3$,ppm): 8.84 (d, 1H), 8.41 (d, 1H), 8.21-7.95 (m, 4H), 7.90 (d, 1H), 7.74 (m, 3H), 7.52 (t, 1H), 7.44 (s, 1H), 7.38 (t, 2H), 7.25-7.10 (m, 5H), 7.04 (t, 1H), 6.87 (d, 1H), 6.72 (t, 1H), 6.45-6.32 (m, 3H), 6.05 (d, 1H), 5.90 (d, 1H), 5.32-5.16 (d, 2H).

EXAMPLE 2
Synthesis of Compound Represented by Formula 6
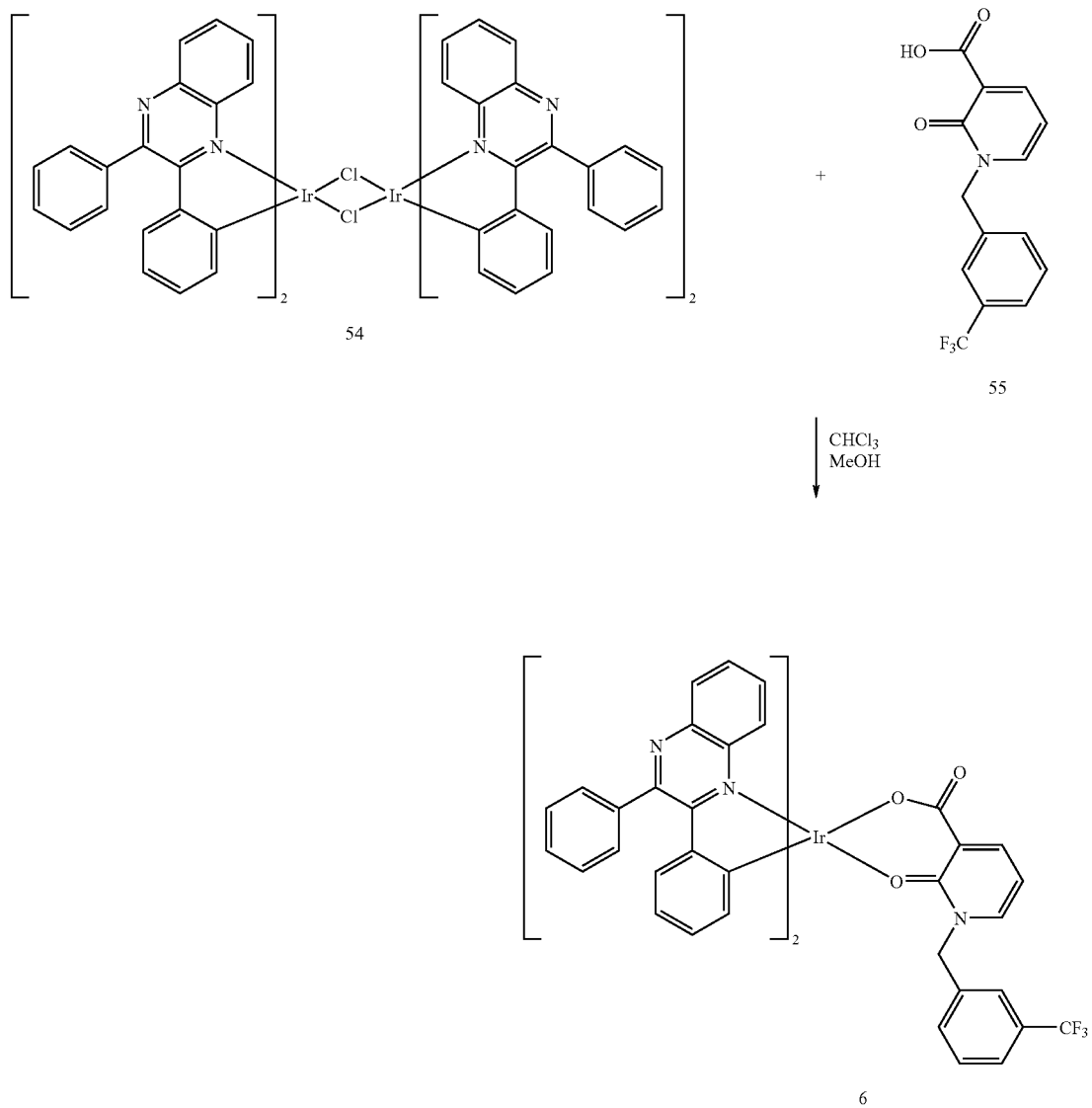
<Reaction Scheme 7>
As illustrated in Reaction Scheme 7, the compound represented by Formula 6 was synthesized in the same manner as in Example 1, except that a 2,3-quinoxaline iridium dimer of Formula 54 was used instead of a 2,3-(4-fluoro)-quinoxaline iridium dimer.

EXAMPLE 3

Synthesis of Compound Represented by Formula 7

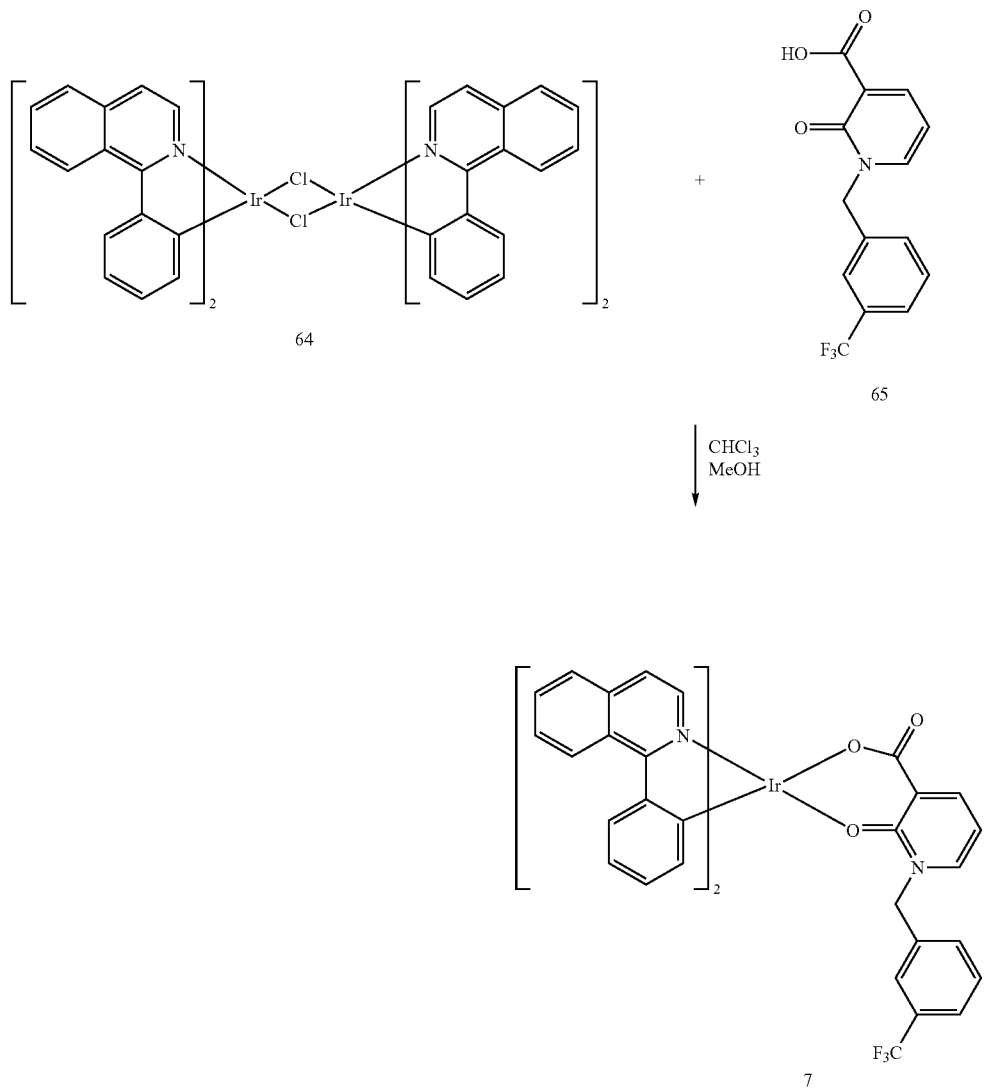

As illustrated in Reaction Scheme 8, the compound represented by Formula 7 was synthesized in the same manner as in Example 1, except that a 1-phenylisoquinoline iridium dimer of Formula 64 was used instead of a 2,3-(4-fluoro)-quinoxaline iridium dimer. The structure of the final product was identified using a $^1$H NMR spectrum:

$^1$H-NMR(CD$_2$Cl$_2$,ppm): 8.96 (d, 2H), 8.86 (d, 2H), 8.15 (t, 2H), 7.85 (d, 1H), 7.80-7.61 (m, 5H), 7.60 (d, 1H), 7.45 (d, 1H), 7.22 (d, 2H), 7.09 (d 1H), 7.04-6.88 (m, 2H), 6.83 (t, 1H), 6.72 (t, 2H), 6.63-6.55 (m, 3H), 6.37 (d, 1H), 6.20 (d, 1H), 5.30 (d, 2H).

EXAMPLE 4
Synthesis of Compound Represented by Formula 8
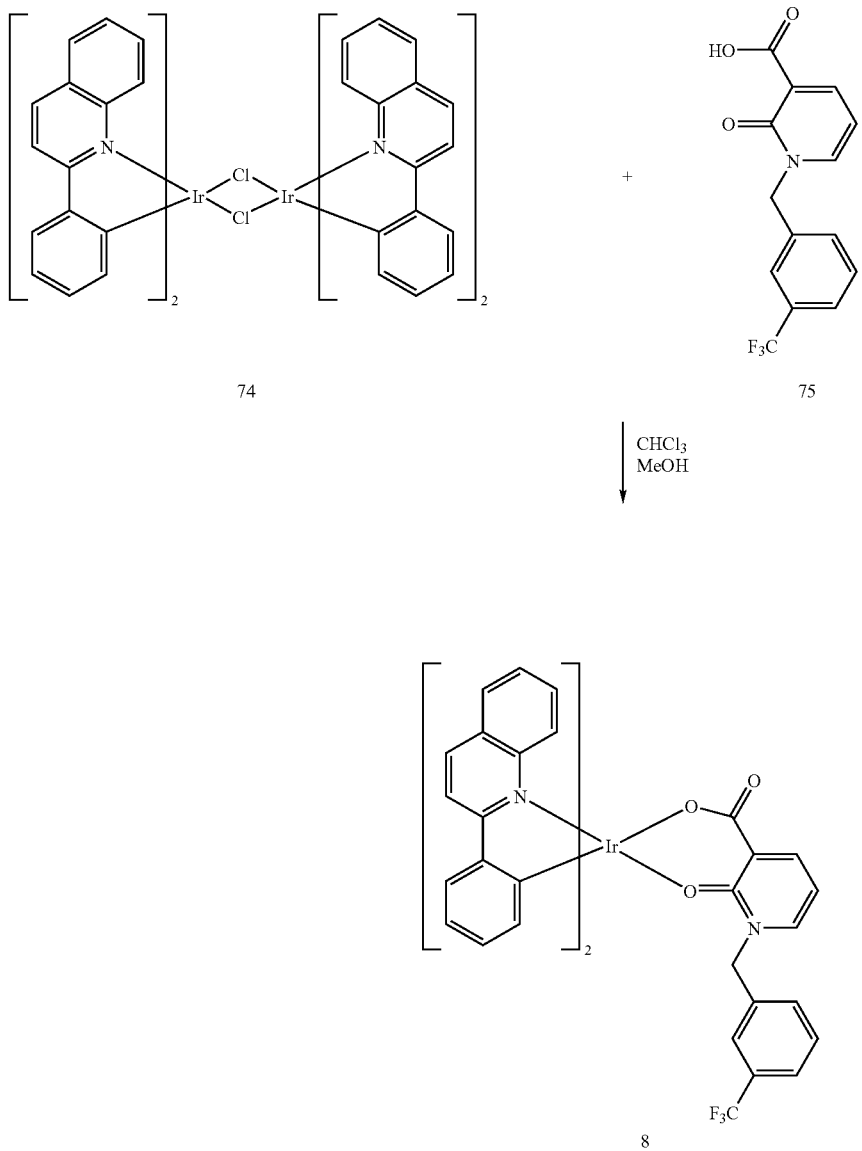
<Reaction Scheme 9>
As illustrated in Reaction Scheme 9, the compound represented by Formula 8 was synthesized in the same manner as in Example 1, except that a 2-phenylisoquinoline iridium dimer of Formula 74 was used instead of a 2,3-(4-fluoro)-quinoxaline iridium dimer.

EXAMPLE 5

Synthesis of Compound Represented by Formula 9

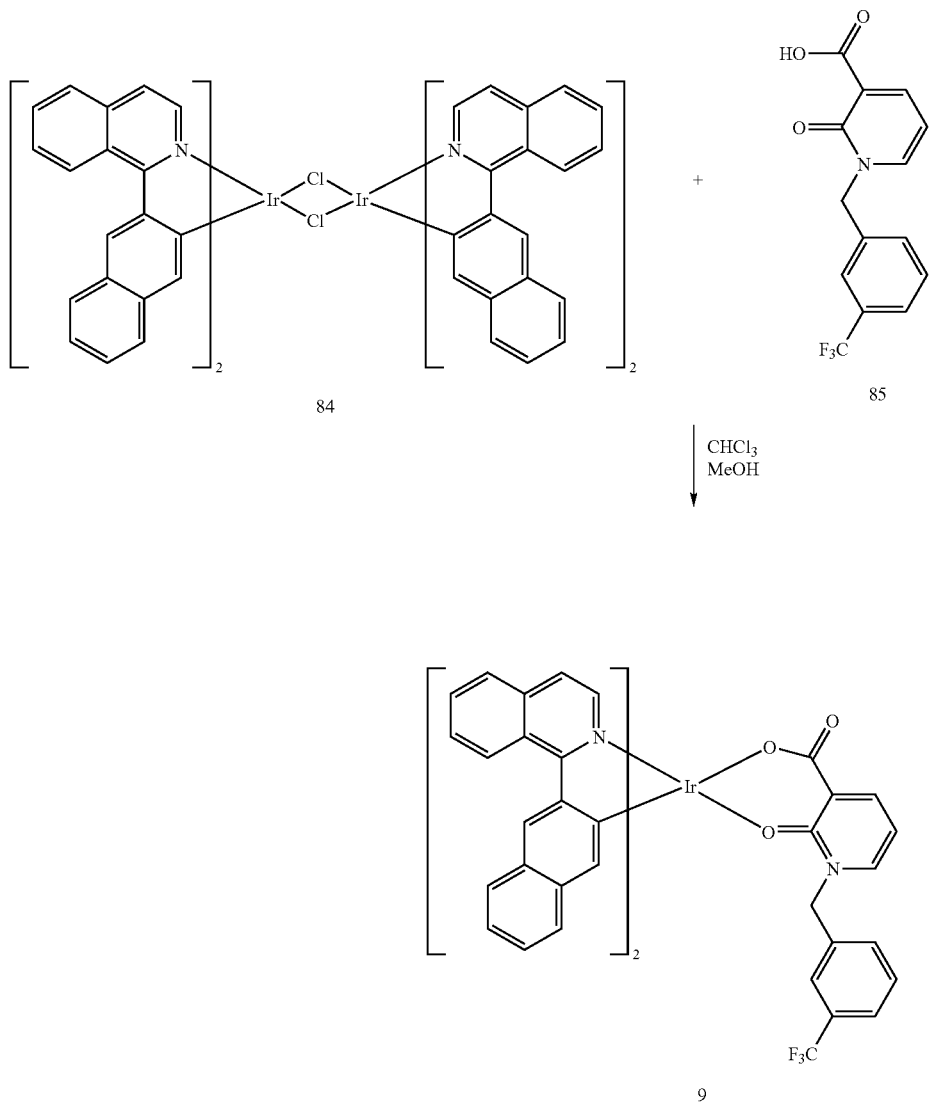

<Reaction Scheme 10>

The compound represented by Formula 9 was synthesized in the same manner as in Example 1, except that a 1-naphthylisoquinoline iridium dimer of Formula 84 was used instead of a 2,3-(4-fluoro)-quinoxaline iridium dimer. The structure of the final product was identified using a $^1$H NMR spectrum:

$^1$H-NMR(CD$_2$Cl$_2$,ppm): 9.19 (d, 2H), 9.11 (d, 1H), 8.92 (d, 1H), 8.70 (d, 1H), 8.74 (s, 2H), 8.02-7.95 (m, 4H), 7.88-7.80 (m, 3H), 7.63 (d, 1H), 7.60 (d, 1H), 7.30(d, 2H), 7.21 (m, 4H), 7.16 (t, 2H), 6.72 (t, 1H), 6.66 (d, 2H), 6.59 (t, 3H), 6.37 (d, 1H), 5.28 (d, 2H).

The compounds represented by Formulas 5 through 9 obtained according to Examples 1 through 5 were dissolved in methylene chloride to prepare $10^{-4}$ M solutions, and photoluminescence characteristics of these solutions were measured. In addition, such solutions were spin coated on neat films and photoluminescence characteristics of the coated films were measured.

The photoluminescence characteristics and color coordinates (CIE) of the compounds represented by Formulas 5 through 9 which are obtained as shown in Examples 1 to 4 are shown in Table 1:

TABLE 1

| | PL characteristic $\lambda_{max}$ (nm) | | CIE (x, y) | |
|---|---|---|---|---|
| | Solution | Film | Solution | Film |
| Example 1: | 627 | 638 | (0.68, 0.31) | (0.67, 0.32) |
| Example 2: | 655 | 655 | (0.69, 0.30) | (0.69, 0.30) |
| Example 3 | 635 | — | (0.609, 0.30) | — |

TABLE 1-continued

| | PL characteristic $\lambda_{max}$ (nm) | | CIE (x, y) | |
|---|---|---|---|---|
| | Solution | Film | Solution | Film |
| Example 4 | 610 | — | (0.60, 0.39) | — |
| Example 5 | 640 | — | (0.67, 0.32) | — |

As illustrated in Table 1, dopants containing an oxo-pyridine carboxylate as an ancillary ligand having excellent phosphorescent characteristics are formed. In particular, the introduction of the substituent results in a strong electronic effect, and thus, the dopant is suitable to be used to form a phosphorescent material that emits light of a wavelength corresponding to red light.

Figure 3:
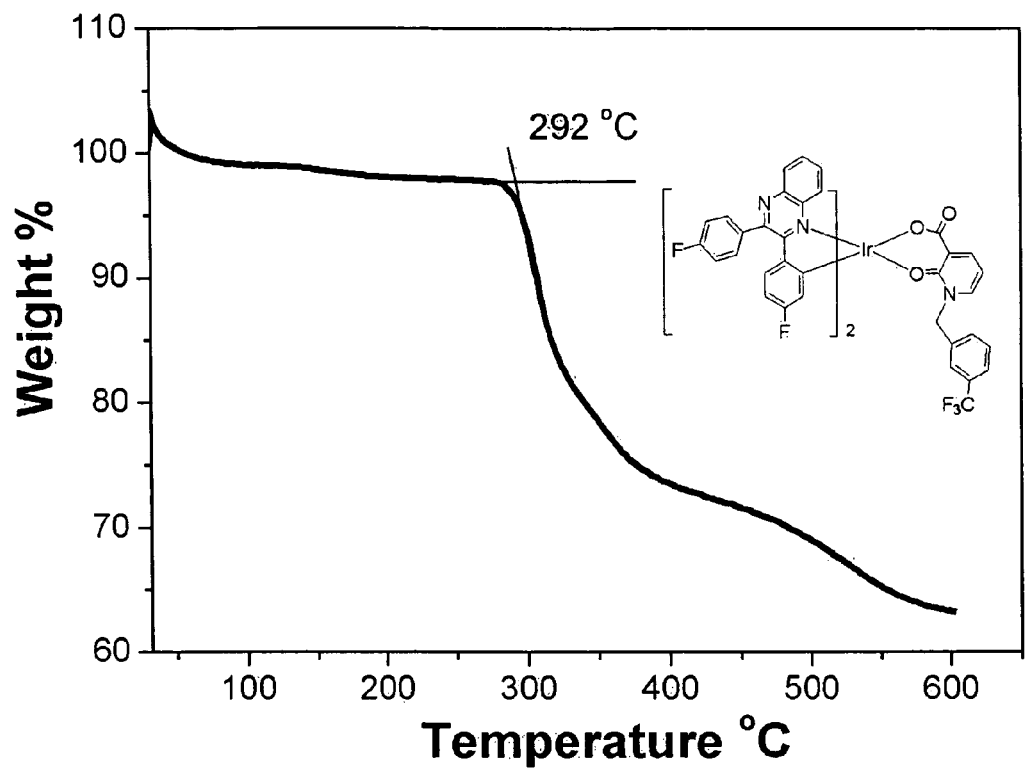
FIG. 3 is a graph showing the result of a thermogravimetry analysis of an organometallic complex obtained in Example 1.
Figure 4:
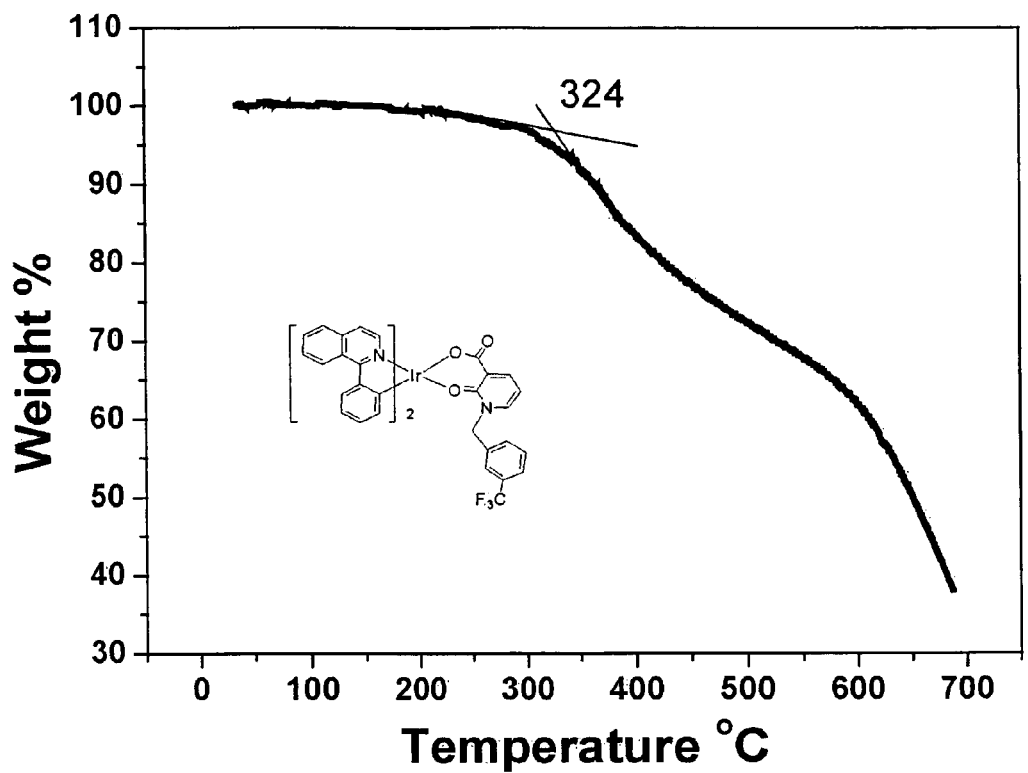
FIG. 4 is a graph showing the result of a thermogravimetric analysis of an organometallic complex obtained in Example 3.

In particular, thermogravimetry was performed on organometallic complexes obtained in Examples 1 and 3 and the results are shown in FIGS. 3 and 4. Referring to FIGS. 3 and 4, the decomposition temperature of the organometallic complexes of Examples 1 and 3 are 292° C. and 324° C., respectively, showing excellent thermal stability. Such thermal stability has an excellent property which endures plasticity while a device is manufactured.

Manufacture of Organic Electroluminescent (EL) Devices

EXAMPLE 6

An indium-tin oxide (ITO)-coated transparent electrode substrate was washed, and an ITO electrode pattern was formed on the substrate using a photoresist resin and an etchant. The ITO electrode patterned substrate was again washed. PEDOT{poly(3,4-ethylenedioxythiophene)}[AI 4083]-PSS was coated on the washed ITO electrode patterned substrate to a thickness of about 50 nm and baked at 120° C. for about 5 minutes to form a hole injection layer.

A mixture solution, which was prepared by mixing PVK, CBP (PVK:CBP=4:5) and 8% by weight of the dopant of Formula 5 with chloroform, was spin coated on the hole injection layer to form a light emitting layer with a thickness of 85 nm. Then, aluminum(III)bis(2-methyl-8-quinolinato)$_4$-phenylphenolate (Balq) was vacuum deposited to a thickness of 20 nm on the polymer light emitting layer using a vacuum deposition device under a pressure of $4 \times 10^{-6}$ torr or less and tris-8-hydroxyquinoline aluminum (Alq$_3$) was vacuum deposited to form an electron transport layer with a thickness of 15 nm. Then, LiF was vacuum deposited on the electron transport layer at a speed of 0.1 nm/sec to form an electron injection layer with a thickness of 1 nm.

Figure 2:
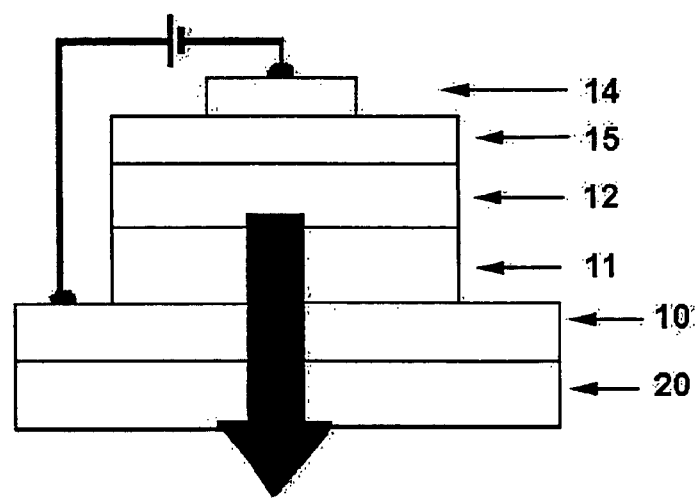
FIG. 2 is a diagram illustrating an organic electroluminescent device manufactured according to an embodiment of the present invention.

Subsequently, Al was deposited at a speed of 10 Å/sec to form an anode with a thickness of 150 nm and the resultant structure was encapsulated, thereby completing manufacture of the organic EL device. Here, the encapsulating process was performed by sealing the resultant structure of the Al deposition in a glove box in which BaO powder was present in a dry nitrogen gas atmosphere and by final treating by UV hardener. The structure of the device is ITO/PEDOT-PSS (50 nm)/PVK-CBP (4:5)-dopant 8% by weight (85 nm)/Balq (20 nm)/Alq$_3$ (15 nm)/LiF (1 nm)/Al(150 nm). The organic EL device had a multi-layer structure and its schematic view is illustrated in FIG. 2. In this case, the light emitting area of the organic EL device was 6 mm$^2$.

EXAMPLE 7

An organic EL device was manufactured in the same manner as in Example 6, except that the compound represented by Formula 6 (synthesized in Example 2) was used instead of the compound represented by Formula 5 (synthesized in Example 1).

EXAMPLE 8

An organic EL device was manufactured in the same manner as in Example 6, except that the compound represented by Formula 7 (synthesized in Example 3) was used instead of the compound represented by Formula 5 (synthesized in Example 1).

EXAMPLE 9

An organic EL device was manufactured in the same manner as in Example 6, except that the compound represented by Formula 8 (synthesized in Example 2) was used instead of the compound represented by Formula 5 (synthesized in Example 1).

EXAMPLE 10

An organic EL device was manufactured in the same manner as in Example 6, except that the compound represented by Formula 9 (synthesized in Example 5) was used instead represented by the compound represented by Formula 5 (synthesized in Example 1).

EXAMPLE 11

An organic EL device was manufactured in the same manner as in Example 6, except that 8% by weight of the compound represented by Formula 5 was used instead of 5% by weight of the compound represented by Formula 5.

Photoluminescence characteristics, color coordinates (CIE), current efficiency, operating voltage, and brightness of organic electroluminescent (EL) devices obtained in Examples 8 and 11 are shown in Table 2.

TABLE 2

| | EL $\lambda_{max}$ (nm) | CIE (x, y) | Current efficiency | Operating voltage (V) | Maximum brightness (cd/m$^2$) |
|---|---|---|---|---|---|
| Example 8 | 631 | (0.64, 0.32) | 0.89 at 27.4 mA/cm$^2$ | 7.0 | 1147 at 16.5 V 215 mA/cm$^2$ |
| Example 11 | 631 | (0.65, 0.32) | 2.17 at 6.23 mA/cm$^2$ | 7.0 | 1134 at 15.2 V and 205 mA/cm$^2$ |

As illustrated in Table 2, the organic electroluminescent device including the compound according to the embodiment of the present invention shows high brightness in a wavelength corresponding to red light emitting region and high current density even in a low voltage, and can also operate even in a low voltage.

An organometallic complex according to the embodiment of the present invention can effectively emit light of a wavelength corresponding to red light. The organometallic complex is suitable to form an organic layer of an organic EL device, and emits light in a wavelength range of 550 to 650 nm as efficient phosphorescent materials. In addition, when the organometallic complex is used with a green phosphorescent material or a blue phosphorescent material, a white light can be emitted.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic complex represented by Formula 3:

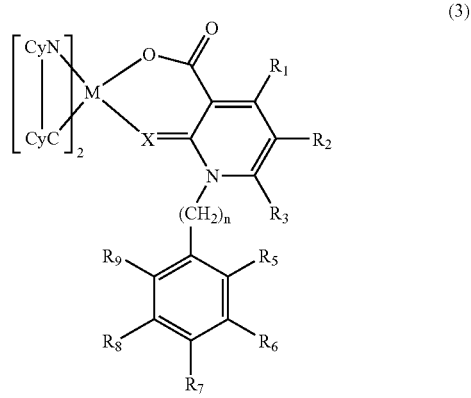

(3)

M is Ir, Os, Pt, Pb, Re, Ru or Pd and has oxidation state of 3;

CyN is a substituted or unsubstituted $C_3$-$C_{60}$ heterocyclic group including nitrogen which is combined with M, 1,2,4-triazole including nitrogen which is combined with M, or a substituted or unsubstituted $C_3$-$C_{60}$ heteroaryl group including nitrogen which is combined with M;

CyC is a substituted or unsubstituted $C_4$-$C_{60}$ cyclic group including carbon which is combined with M, a substituted or unsubstituted $C_3$-$C_{60}$ heterocyclic group including carbon which is combined with M, a substituted or unsubstituted $C_6$-$C_{60}$ aryl group including carbon which is combined with M, or a substituted or unsubstituted $C_3$-$C_{60}$ heteroaryl group including carbon which is combined with M;

CyN—CyC indicates a cyclometalating ligand which is a monoanionic bidentate ligand and combined with M through the nitrogen (N) of the CyN and the carbon (C) of the CyC;

X is $NR_0$, O, or S, where $R_0$ is hydrogen, a halogen atom, a carboxyl group, or a $C_1$-$C_{20}$ alkyl group;

$R_1$, $R_2$, $R_3$, $R_5$, $R_6$, $R_7$, $R_8$, and $R_9$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_3$-$C_{30}$ heteroaryl group, or a substituted or unsubstituted $C_3$-$C_{30}$ heteroarylalkyl group and at least two of $R_1$, $R_2$, $R_3$, $R_5$, $R_6$, $R_7$, $R_8$, and $R_9$ may be fused into a 5 to 7-membered ring; and n is an integer in a range of 0 to 30.

2. The organometallic complex of claim 1, wherein the complex represented by Formula 3 is represented by one of Formulas 5 through 9:

(5)

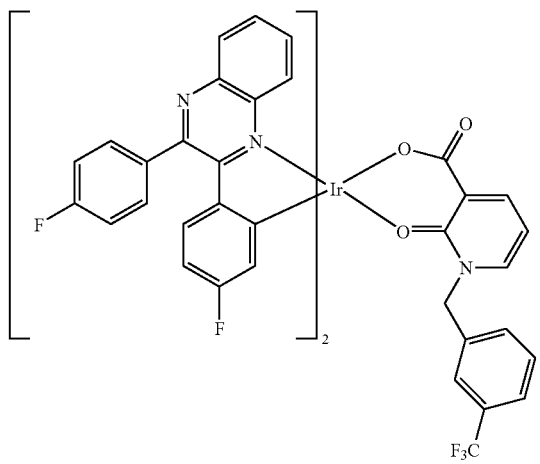

(6)

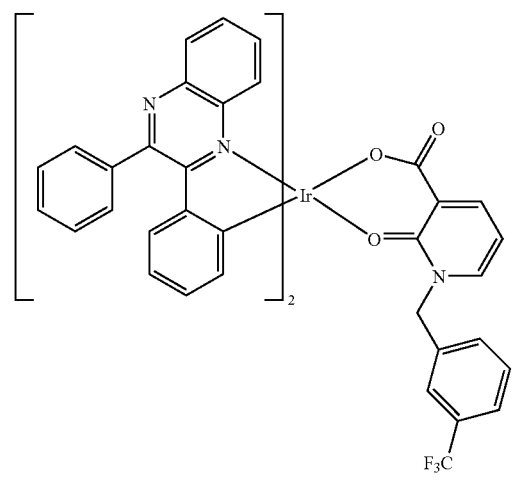

(7)

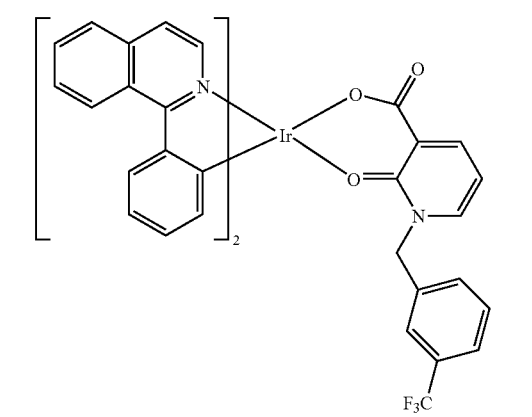

(8)

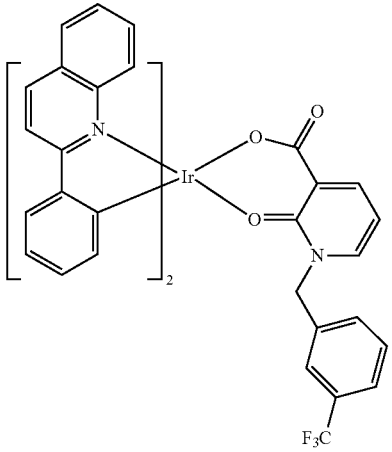

(9)

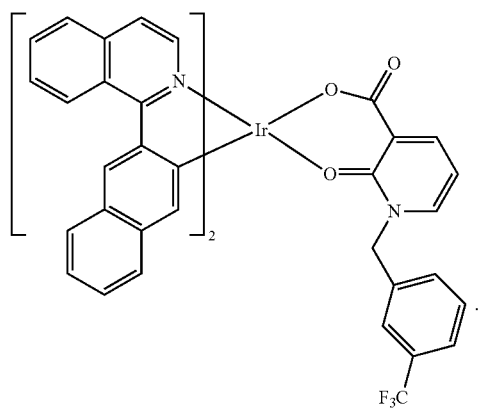

3. The organometallic complex of claim 1, the cyclometalating ligand (CyN—CyC) being represented by one of Formulas 12, 13 and 15 through 39:

(12)

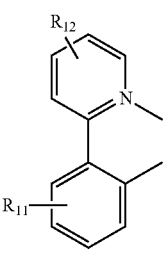

(13)

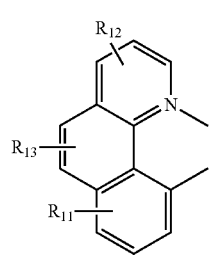

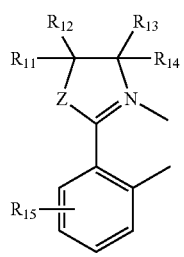
(15)
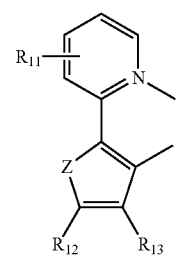
(16)
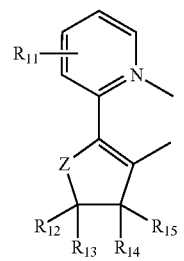
(17)
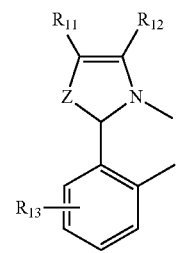
(18)
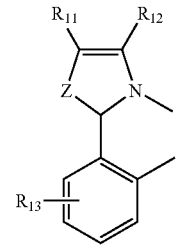
(18)
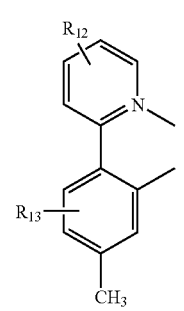
(19)
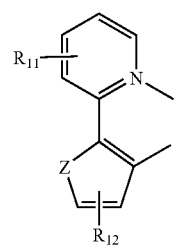
(20)
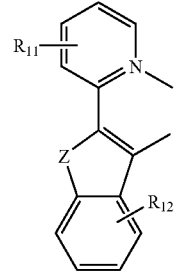
(21)
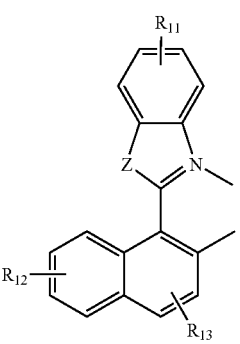
(22)
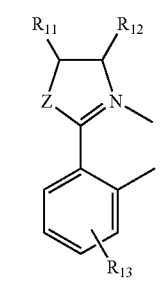
(23)
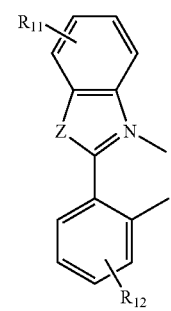
(24)

-continued
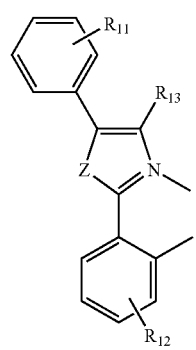 (25)
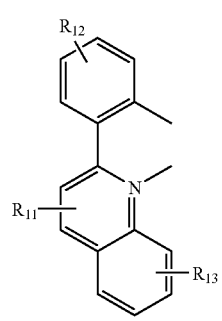 (26)
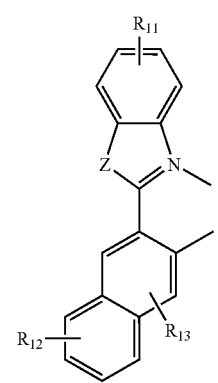 (27)
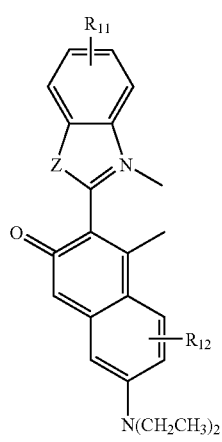 (28)
-continued
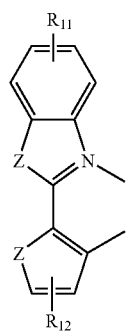 (29)
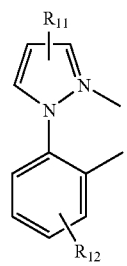 (30)
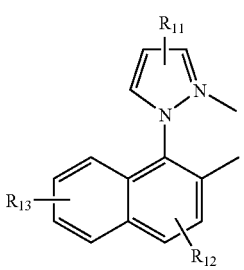 (31)
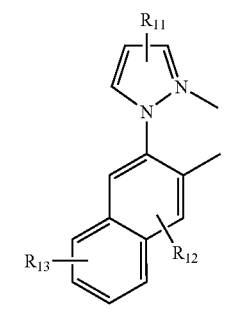 (32)
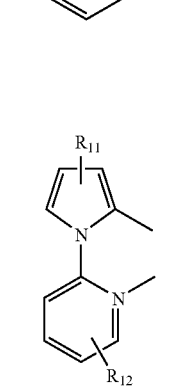 (33)

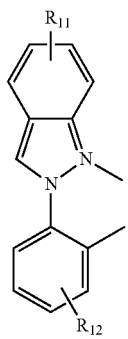 (34)

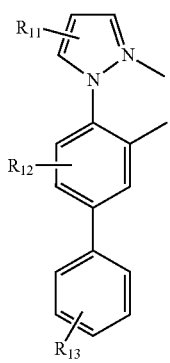 (35)

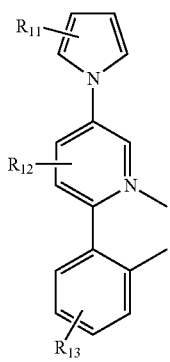 (36)

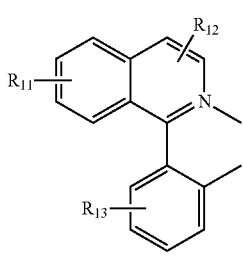 (37)

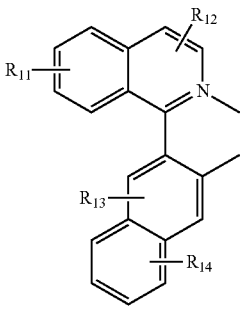 (38)

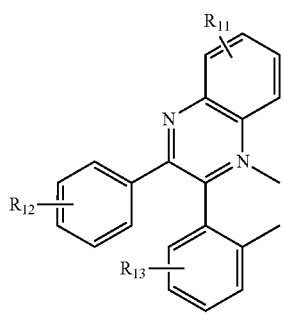 (39)

where $R_{11}$, $R_{12}$, $R_{13}$, $R_{14}$, and $R_{15}$ are each independently hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, or a $C_6$-$C_{20}$ aryl group, where R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_3$-$C_{40}$ heteroaryl group, and a substituted or unsubstituted $C_3$-$C_{40}$ heteroarylalkyl group; and Z is S, O, or NR$_0$, where R$_0$ is hydrogen or a $C_1$-$C_{20}$ alkyl group.

4. The organometallic complex of claim 1, wherein the substituted or unsubstituted $C_3$-$C_{60}$ heterocyclic group of the CyN is selected from the group consisting of pyrrolidine, morpholine, thiomorpholine, and thiazolidine, the substituted or unsubstituted $C_3$-$C_{60}$ heteroaryl group of CyN is selected from the group consisting of pyridine, 4-methoxypyridine, quinoline, pyrrole, indole, pyrazine, pyrazole, imidazole, pyrimidine, quinazoline, thiazole, oxazole, and triazine; and the substituted or unsubstituted $C_4$-$C_{60}$ cyclic group of the CyC is selected from the group consisting of cyclohexane and cyclopentane, the substituted or unsubstituted $C_3$-$C_{60}$ heterocyclic group of the CyC is selected from the group consisting of tetrahydrofuran, 1,3-dioxane, 1,3-dithiane, 1,3-dithiolane, 1,4-dioxa- 8-azaspiro [4,5] decane, and 1,4-dioxaspiro[4,5]decan-2-one, the substituted or unsubstituted $C_6$-$C_{60}$ aryl group of the CyC is selected from the group consisting of phenyl, 1,3-benzodioxole, biphenyl, naphthalene, anthracene, and azulene, and the substituted or unsubstituted $C_3$-$C_{60}$ heteroaryl group of the CyC is selected from the group consisting of thiophene, furan2(5H)-furanone, pyridine, coumarin, imidazole, 2-phenylpyridine, 2-benzothiazole, 2-benzooxazole, 1-phenylpyrazole, 1-naphthylpyrazole,5-(4-methoxyphenyl) pyrazole, 2,5-bisphenyl-1,3,4-oxadiazole, and 2,3-benzofuran2-(4-biphenyl)-6-phenyl benzooxazole.

5. The organometallic complex of claim 1, M being one of Ir and Pt.

6. An organic electroluminescence device having an organic layer interposed between a pair of electrodes, the organic layer comprising the organometallic complex of claim 1.

7. An organic electroluminescence device, comprising:
a first electrode;
a second electrode; and
an organic layer comprising a light emitting layer comprised of an organometallic complex represented by Formula 3:

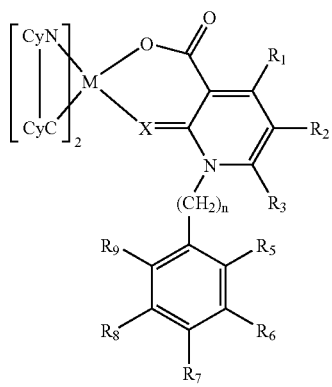

(3)

where M is Ir, Os, Pt, Pb, Re, Ru or Pd and has oxidation state of 3;
CyN is a substituted or unsubstituted $C_3$-$C_{60}$ heterocyclic group including nitrogen which is combined with M, 1,2,4-triazole including nitrogen which is combined with M, or a substituted or unsubstituted $C_3$-$C_{60}$ heteroaryl group including nitrogen which is combined with M;
CyC is a substituted or unsubstituted $C_4$-$C_{60}$ cyclic group including carbon which is combined with M, a substituted or unsubstituted $C_3$-$C_{60}$ heterocyclic group including carbon which is combined with M, a substituted or unsubstituted $C_3$-$C_{60}$ aryl group including carbon which is combined with M, or a substituted or unsubstituted $C_3$-$C_{60}$ heteroaryl group including carbon which is combined with M;
CyN—CyC indicates a cyclometalating ligand which is a monoanionic bidentate ligand and combined with M through the nitrogen (N) of the CyN and the carbon (C) of the CyC;
X is $NR_0$, O, or S, where $R_0$ is hydrogen, a halogen atom, a carboxyl group, or a $C_1$-$C_{20}$ alkyl group;
$R_1$, $R_2$, $R_3$, $R_5$, $R_6$, $R_7$, $R_8$, and $R_9$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_3$-$C_{30}$ heteroaryl group, or a substituted or unsubstituted $C_3$-$C_{30}$ heteroarylalkyl group and at least two of $R_1$, $R_2$, $R_3$, $R_5$, $R_6$, $R_7$, $R_8$, and $R_9$ may be fused into a 5 to 7 membered ring; and n is an integer in a range of 0 to 30.

8. The organic electroluminescence device of claim 7, the organometallic complex being represented by one of Formulae 5 through 9:

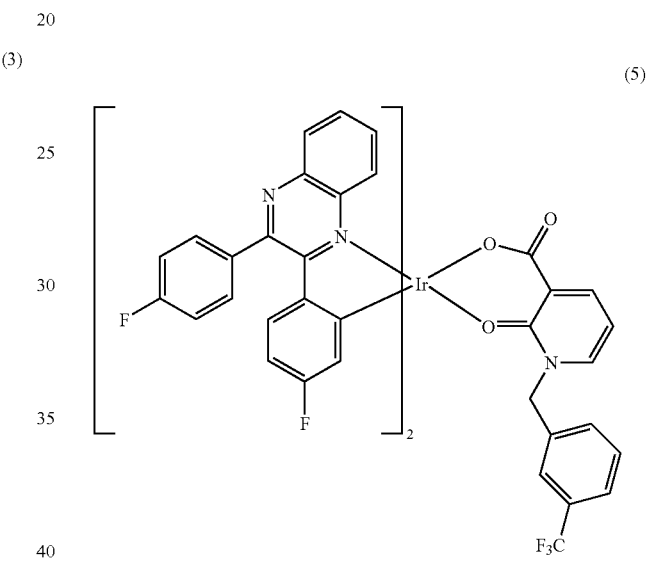

(5)

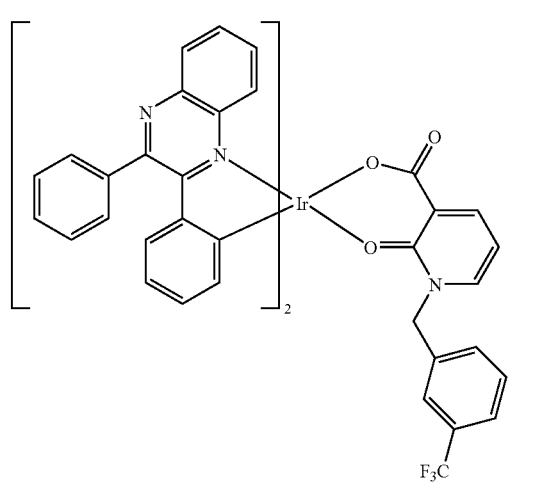

(6)

(7)

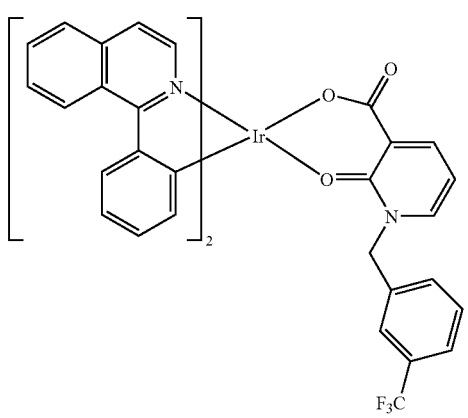

(8)

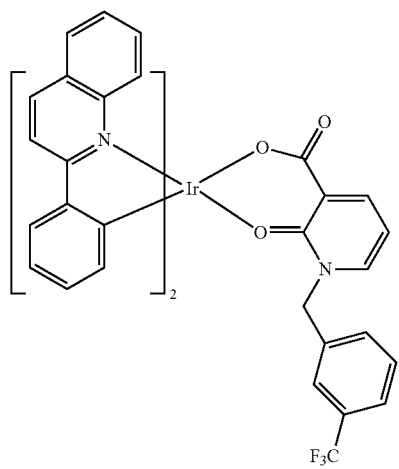

(9)

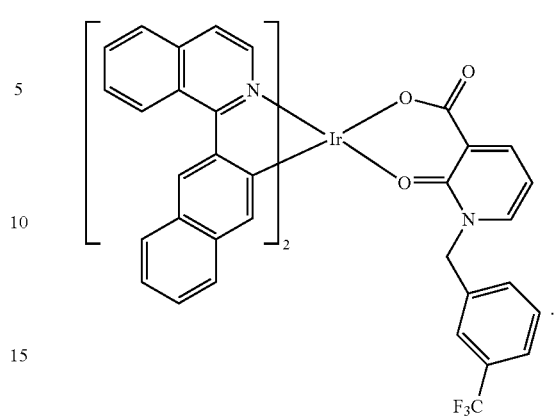

9. The organic electroluminescence device of claim 7, the organometallic complex being in an amount of 1 to 30 parts by weight based on 100 parts by weight of materials used to form the light emitting layer.

10. The organic electroluminescence device of claim 7, the light emitting layer further comprising at least one of green phosphorescent material and blue phosphorescent material.

11. The organic electroluminescence device of claim 7, the light emitting layer further comprising at least one host selected from the group consisting of a polymer host, a mixture host comprising a polymer and a small molecule, a small molecule host, and a non-emitting polymer matrix.

* * * * *